(12) United States Patent
Gerber et al.

(10) Patent No.: US 8,032,229 B2
(45) Date of Patent: *Oct. 4, 2011

(54) THERAPY ADJUSTMENT

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/815,834

(22) Filed: Jun. 15, 2010

(65) Prior Publication Data

US 2010/0256592 A1  Oct. 7, 2010

Related U.S. Application Data

(63) Continuation of application No. 11/799,035, filed on Apr. 30, 2007, now Pat. No. 7,769,464.

(51) Int. Cl.
*A61N 1/00* (2006.01)

(52) U.S. Cl. .................. 607/62; 607/59; 607/2

(58) Field of Classification Search .......... 607/59
See application file for complete search history.

(56) References Cited

U.S. PATENT DOCUMENTS

| | | | |
|---|---|---|---|
| 4,566,456 A | 1/1986 | Koning et al. | |
| 5,040,534 A | 8/1991 | Mann et al. | |
| 5,158,078 A | 10/1992 | Bennett et al. | |
| 5,741,310 A | 4/1998 | Wittkampf | |
| 6,393,325 B1 | 5/2002 | Mann et al. | |
| 6,937,900 B1 | 8/2005 | Pianca et al. | |
| 7,313,440 B2 | 12/2007 | Miesel | |
| 7,403,820 B2 | 7/2008 | DiLorenzo | |
| 7,406,351 B2 | 7/2008 | Wesselink | |
| 7,519,431 B2 | 4/2009 | Goetz et al. | |
| 2005/0060001 A1 | 3/2005 | Singhal et al. | |
| 2005/0228455 A1 | 10/2005 | Kramer et al. | |
| 2005/0245988 A1 | 11/2005 | Miesel | |
| 2006/0259099 A1 | 11/2006 | Goetz et al. | |
| 2008/0269843 A1 | 10/2008 | Gerber et al. | |

OTHER PUBLICATIONS

U.S. Appl. No. 11/414,625, entitled, "Closed-Loop Therapy Adjustment" and filed on Apr. 28, 2006.
U.S. Appl. No. 11/607,454, entitled, "Closed-Loop Therapy Adjustment" and filed on Dec. 1, 2006.
U.S. Appl. No. 11/607,426, entitled, "Closed-Loop Therapy Adjustment" and filed on Dec. 1, 2006.
U.S. Appl. No. 11/779,112, entitled, "Therapy Adjustment" and filed on Apr. 30, 2007.

(Continued)

*Primary Examiner* — Carl H Layno
*Assistant Examiner* — Jeremiah T Kimball
(74) *Attorney, Agent, or Firm* — Shumaker & Sieffert, P.A.

(57) ABSTRACT

Systems and methods for adjusting a therapy delivered to a patient include detecting a value of at least one sensed patient parameter and adjusting a therapy parameter value to accommodate different patient parameter values. A data structure including a plurality of patient parameter values and associated therapy parameter values may be stored within a medical device or a programming device. Upon detecting a patient parameter value, an associated therapy parameter value from the data structure may be selected. If no therapy parameter value is associated with the detected patient parameter value, an intermediate therapy parameter value may be generated by interpolating between the most recently implemented therapy parameter value and a stored therapy parameter value. In some embodiments, the rate of shifting between parameters of two stored or interpolated therapy parameter values may be based on the rate of change of the patient parameter value over time.

25 Claims, 10 Drawing Sheets

OTHER PUBLICATIONS

Notification of Transmittal of the International Search Report and the Written Opinion of the international Searching Authority, or the Declaration, for corresponding patent application No. PCT/2008/060411, mailed Aug. 29, 2008, 13 pages.

Reply to Written Opinion for corresponding patent application No. PCT/2008/060411, filed Feb. 23, 2009, 19 pages.

Office Action for patent application U.S. Appl. No. 11/799,112, mailed Apr. 1, 2009, 15 pages.

Responsive Amendment for patent U.S. Appl. No. 11/799,112, filed Jul. 1, 2009, 14 pages.

Notification of Transmittal of the International Preliminary Report on Patentability for corresponding patent application No. PCT/US2008/060411, mailed Aug. 19, 2009, 11 pages.

Final Office Action for U.S. Appl. No. 11/799,112, mailed Oct. 29, 2009, 14 pages.

Response to Final Office Action for U.S. Appl. No. 11/799,112, filed Dec. 29, 2009, 9 pages.

Final Office Action for U.S. Appl. No. 11/799,035, mailed Nov. 2, 2009, 17 pages.

Response to Final Office Action for patent application No. 11/799,035, filed Jan. 4, 2010, 9 pages.

Office Action for U.S. Appl. No. 11/799,035, mailed Mar. 30, 2009, 19 pages.

Response to Office Action for U.S. Appl. No. 11/799,035, filed Jun. 30, 2009, 14 pages.

U.S. Appl. No. 12/887,237, filed Sep. 21, 2010, Gerber et al.

THERAPY ADJUSTMENT

This application is a continuation of U.S. patent application Ser. No. 11/799,035 filed Apr. 30, 2007, now U.S. Pat. No. 7,769,464, the entire content of which is incorporated herein by reference.

TECHNICAL FIELD

The disclosure relates to medical devices, and more particularly, medical devices that deliver therapy.

BACKGROUND

A variety of types of medical devices are used for chronic, e.g., long-term, provision of therapy to patients. As examples, pulse generators are used for chronic provision of cardiac pacing and neurostimulation therapies, and pumps are used for chronic delivery of therapeutic agents, such as drugs. Typically, such devices provide therapy continuously or periodically according to parameters, e.g., a program comprising respective values for each of a plurality of parameters, specified by a clinician.

In some cases, a medical device may be deliver therapy according to one of a plurality of stored therapy programs. Selections may be made from among the plurality of programs to accommodate different physiological conditions of the patient. For example, the symptoms, e.g., the intensity of pain, of patients who receive spinal cord stimulation (SCS) therapy may vary over time based on the activity level or posture of the patient, the specific activity undertaken by the patient, or the like. Accordingly, different therapy programs may be delivered at different times, depending on the patient activity level or posture.

SUMMARY

In general, the disclosure is directed to techniques for detecting a value of a sensed patient parameter and adjusting a therapy program to accommodate different patient parameter values. In some cases, some therapy programs may be more effective for a particular patient parameter value than other therapy programs. The present disclosure provides techniques for adjusting at least one therapy parameter as a value of a sensed patient parameter changes in order to provide more efficacious therapy for different sensed patient parameter values, such as different patient postures or activity levels. In some embodiments, the patient parameter value may be monitored continuously or substantially continuously, and the therapy parameter may be adjusted as the patient parameter value changes.

Rather than storing an inordinate number of programs for each possible patient parameter value, a limited number of therapy programs are stored and associated with a limited number of patient parameter values. If a sensed patient parameter value is not associated with a stored therapy program, a processor of a medical device, programming device or another computing device implements an algorithm to interpolate between two stored therapy programs to temporarily create a therapy program that provides efficacious therapy for the sensed patient parameter value. In other embodiments, the sensed patient parameter value may be associated with a stored therapy program, and the processor may interpolate between two stored therapy programs to transition therapy delivery according to therapy parameters of a first stored therapy program to therapy parameters according to a second stored therapy program.

In accordance with one embodiment, different therapy programs and associated patient postures are stored within an implantable medical device (IMD). Each therapy program may define one or more therapy parameters such as electrode combinations by which electrical stimulation therapy is delivered, voltage or current amplitude, pulse width or pulse frequency of electrical stimulation, stimulation cycling (e.g., on/off times of an electrical stimulator) or frequency or dosage of drug delivery. When a patient is in a first posture, therapy is delivered according to a first therapy program. A sensor within the IMD or coupled to the IMD (e.g., via wired or wireless communication) detects a change in patient posture. When the sensor senses a second posture of the patient, the IMD may determine whether one of the stored therapy programs is associated with the second posture. If the second posture is associated with a stored therapy program, the IMD implements the associated therapy program. In some embodiments, rather than abruptly changing the therapy delivery via a therapy program associated with a first posture to the therapy program associated with the second posture, IMD may implement an algorithm to create at least one "intermediate" therapy program to gradually adjust therapy between the therapy programs. In one embodiment, one or more intermediate therapy programs are determined by interpolating between the parameters in the first and second therapy programs. The interpolation algorithm may be linear or nonlinear. In one embodiment, the rate of change between the first and second therapy programs is based on the rate of change of the patient's movement between the first and second postures.

If no therapy program is associated with the second posture, the IMD may implement an algorithm to interpolate between the therapy program associated with the first posture and a therapy program associated with a posture that is closest to the second posture. Again, the algorithm may be linear or nonlinear. In this way, the IMD may create a therapy program for the second posture. The rate of change of adjustment of therapy from the first therapy program associated with the first posture to the interpolated program may also be dictated by the rate of change of the patient's movement between the first and second postures, or the rate of change of another patient parameter value that is associated with the therapy programs.

In embodiments, the rate of adjusting between a first therapy program and a second therapy program, or one or more therapy parameters of the first and second therapy programs, may be based on the rate of change of the patient parameter value. The first and second therapy program may be any therapy programs, and are not necessarily limited to stored therapy programs or interpolated therapy programs. In one embodiment, the time rate of change of a patient parameter is used to determine the rate of adjusting between two therapy programs. In another embodiment, the time rate of change of two or more patient parameter values are used to determine the rate of adjustment.

In one embodiment, the disclosure is directed to a method comprising sensing a first value of a parameter of a patient, delivering therapy to the patient according to a first therapy program associated with the first value of the patient parameter, detecting a change from the first value of the patient parameter to a second value of the patient parameter, determining a first rate of the change from the first value to the second value of the patient parameter, identifying a second therapy program based on the second value of the patient parameter, and adjusting the delivery of the therapy to the patient from the first therapy program to the second therapy program at a second rate based on the first rate of the change.

In another embodiment, the disclosure is directed to a system comprising a medical device that is configured to deliver a therapy to a patient, a sensor that is configured to sense a parameter of the patient, a memory that stores a data structure comprising a plurality of values of the patient parameter and associated therapy programs, wherein the therapy programs each comprise at least one therapy parameter, and a processor. The processor controls the medical device to deliver the therapy to the patient according to a first therapy program associated with a first value of a patient parameter detected via the sensor, detect a change from the first value of the patient parameter to a second value of the patient parameter, determine a first rate of the change from the first value to the second value of the patient parameter, identify a second therapy program associated with the second value of the patient parameter via the data structure stored within the memory, and control the medical device to adjust the delivery of the therapy to the patient from the first therapy program to the second therapy program at a second rate based on the first rate.

In another embodiment, the disclosure is directed to a computer-readable medium containing instructions. The instructions cause a processor to receive input indicating a first value of a sensed parameter of a patient, identify a first therapy program associated with the first value of the patient parameter, deliver therapy to the patient according to the first therapy program, detect a change from the first value of the patient parameter to a second value of the patient parameter, determine a first rate of change from the first value to the second value of the patient parameter, identify a second therapy program associated with the second value of the patient parameter, and adjust the delivery of the therapy to the patient from the first therapy program to the second therapy program at a second rate based on the first rate of the change.

In another embodiment, the disclosure is directed to a method comprising sensing a first value of a parameter of a patient, delivering therapy to the patient according to a first therapy program associated with the first value of the patient parameter in a data structure comprising a plurality of patient parameter values and associated therapy programs, detecting a change from the first value of the patient parameter to a second value of the patient parameter, identifying a third value of the patient parameter within the data structure that is closest to the second value of the patient parameter, where the third value of the patient parameter is associated with a second therapy program within the data structure, and generating an intermediate therapy program by interpolating at least one therapy parameter between therapy parameters of the first and second therapy programs.

In another embodiment, the disclosure is directed to a system comprising a medical device that is configured to deliver a therapy to a patient, a sensor that is configured to sense a patient parameter of the patient, a memory that stores a data structure comprising a plurality of patient parameter values and associated therapy programs, where the therapy programs each comprise at least one therapy parameter, and a processor. The processor controls the medical device to deliver the therapy to the patient according to a first therapy program associated with a first value of the patient parameter detected via the sensor, detect a change in the first value to a second value of the patient parameter detected via the sensor, identify a third value patient parameter within the data structure that is closest to the second value, wherein the third value is associated with a second therapy program within the data structure, and interpolate at least one therapy parameter between therapy parameters of the first and second therapy programs to generate an intermediate therapy program.

In another embodiment, the disclosure is directed to a computer-readable medium containing instructions. The instructions cause a processor to control a therapy delivery device to receive input indicating a sensed parameter of a patient, associate a first value of the patient parameter with a first therapy program by referencing a data structure comprising a plurality of patient parameter values and associated therapy programs, deliver therapy to the patient according to the first therapy program, detect a change from the first value of the patient parameter to a second value of the patient parameter, identify a third value of the patient parameter within the data structure that is closest to the second value, wherein the third value is associated with a second therapy program within the data structure, and generate an intermediate therapy program by interpolating at least one therapy parameter between therapy parameters of the first and second therapy programs.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
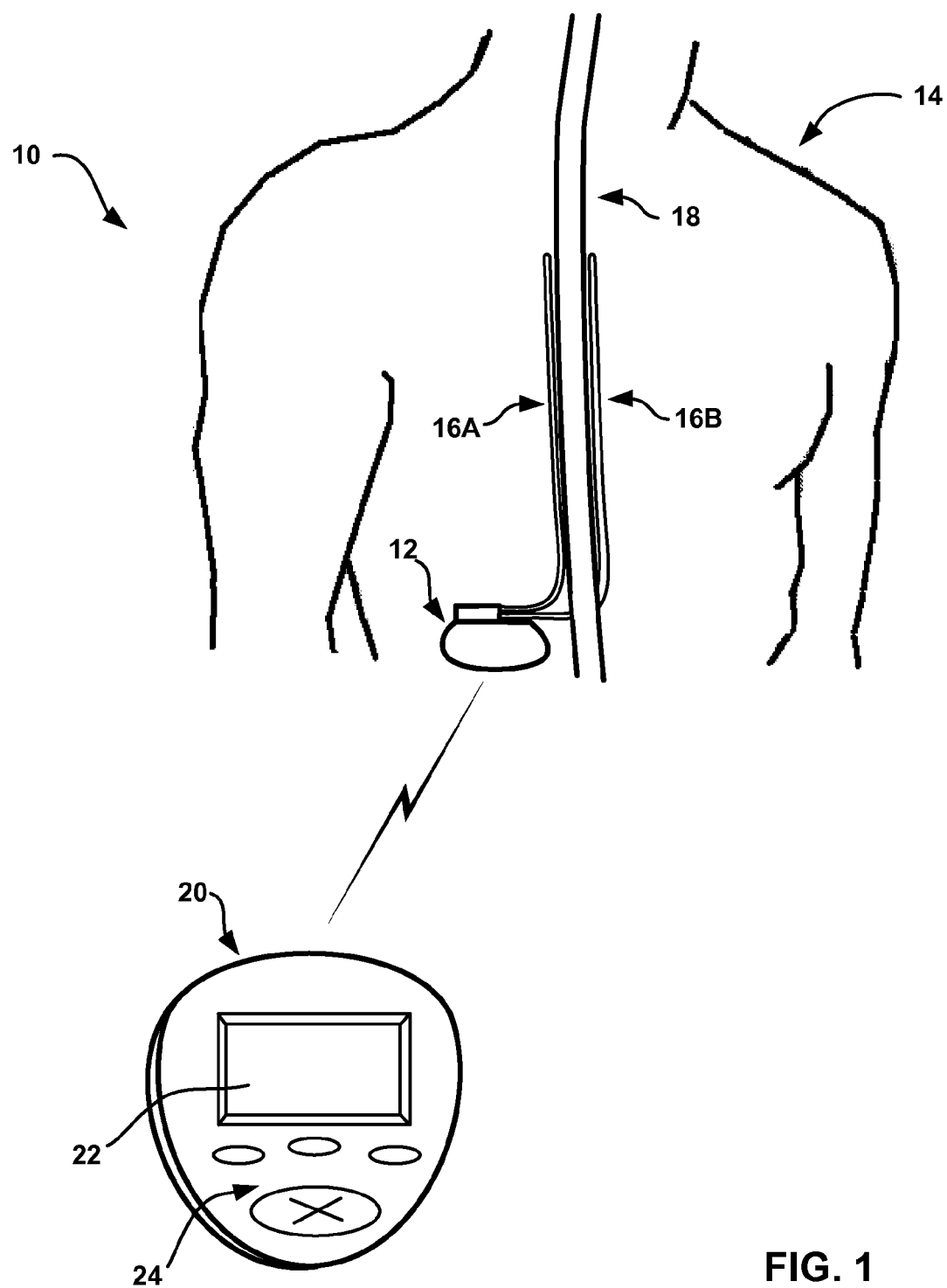
FIG. 1 is a conceptual diagram illustrating an example system that facilitates closed-loop therapy adjustment.

FIG. 1 is a conceptual diagram illustrating an example system 10 that facilitates closed-loop therapy adjustment according to the disclosure. In the illustrated example, system 10 includes an IMD 12, which is implanted within a patient 14, and delivers electrical stimulation therapy to patient 14. In exemplary embodiments, IMD 12 takes the form of an implantable signal generator, and delivers electrical stimulation therapy to patient 14 in the form of a programmable stimulation signal (e.g., in the form of electrical pulses or substantially continuous-time signals).

IMD 12 delivers electrical stimulation therapy to patient 14 via leads 16A and 16B (collectively "leads 16"), and more particularly, via one or more stimulation electrodes carried by leads 16. Leads 16 may also carry one or more sensing electrodes. Leads 16 may, as shown in FIG. 1, be implanted proximate to the spinal cord 18 of patient 14, and IMD 12 may deliver spinal cord stimulation (SCS) therapy to patient 14 in order to, for example, reduce pain experienced by patient 14. However, the disclosure is not limited to the configuration of leads 16 shown in FIG. 1 or the delivery of SCS therapy. For example, one or more leads 16 may extend from IMD 12 to the brain (not shown) of patient 14, and IMD 12 may deliver deep brain stimulation (DBS) therapy to patient 14 to, for example, treat tremor, Parkinson's disease, epilepsy or other movement disorders or other neurological disorders. As further examples, one or more leads 16 may be implanted proximate to the pelvic nerves (not shown), stomach (not shown), or sexual organs (not shown) and IMD 12 may deliver electrical stimulation therapy to treat urinary or fecal incontinence, gastroparesis, sexual dysfunction, peripheral neuropathy, post-operative pain mitigation, ilioinguinal nerve stimulation, intercostal nerve stimulation, gastric stimulation for the treatment of gastric mobility disorders and obesity or muscle stimulation (e.g., functional electrical stimulation (FES) of muscles).

Further, as discussed above, the disclosure is not limited to embodiments in which IMD 12 delivers stimulation therapy. For example, in some embodiments, IMD 12 may additionally or alternatively be coupled to one or more catheters to deliver one or more therapeutic substances to patient 14, e.g., one or more drugs. Additionally, the disclosure is not limited to implanted devices. Any implantable or external medical device may deliver closed-loop therapy according to the techniques of the disclosure.

IMD 12 includes a sensor that is configured to sense at least one patient parameter. The patient parameter may include parameters that may affect the efficacy of therapy or indicate a parameter that affects the efficacy of therapy, e.g., activity, activity level, posture, or a physiological parameter of patient 14. Physiological parameters may include heart rate, respiration rate, respiratory volume, core temperature, blood pressure, blood oxygen saturation, partial pressure of oxygen within blood, partial pressure of oxygen within cerebrospinal fluid, muscular activity, arterial blood flow, electromyogram (EMG), an electroencephalogram (EEG), an electrocardiogram (ECG) or galvanic skin response. In other embodiments, a sensor used to sense such patient parameters may be implanted at a site within patient 14 or worn on the exterior of the patient, in which case the sensor may be coupled to IMD 12. An example sensor is a 3-axis accelerometer located within IMD 12. Patient parameter values detected by IMD 12 based on the signals generated by such a sensor may correspond to an activity or posture undertaken by patient 14, or a gross level of physical activity, e.g., activity counts based on footfalls or the like. For example, IMD 12 may associate the signal generated by a 3-axis accelerometer or multiple single-axis accelerometers (or a combination of a three-axis and single-axis accelerometers) with a patient posture, such as sitting, recumbent, upright, and so forth.

In exemplary embodiments, IMD 12 delivers therapy according to a therapy program selected from two or more stored therapy programs, or an intermediate therapy program generated by interpolating between two therapy programs, where at least one is a stored therapy program. In particular, IMD 12 may select a therapy program or interpolate between two stored therapy programs based on the value of a sensed patient parameter. Different therapy programs may provide efficacious therapy for different physiological conditions of the patient. For example, the symptoms, e.g., the intensity of pain, of patients who receive spinal cord stimulation (SCS) therapy may vary over time based on the activity level or posture of the patient, the specific activity undertaken by the patient, or the like. Accordingly, IMD 12 may select different therapy programs for delivery at different times, depending on a sensed patient parameter value, which may be, for example, the patient activity level or posture of patient 14.

A therapy program may be defined by a set of one or more therapy parameters that define an aspect of the therapy delivered by IMD 12. For example, a program that controls delivery of stimulation by IMD 12 in the form of pulses may define a voltage or current pulse amplitude, a rate of an amplitude change (e.g., ramping up or down of stimulation amplitudes), a pulse width, a pulse rate, for stimulation pulses delivered by IMD 12, a cycle of stimulation delivery (e.g., a timing of when IMD 12 is in an on mode or an off/sleep mode) and so forth. Further, each of leads 16 includes electrodes (not shown in FIG. 1), and the parameters for a program that controls delivery of stimulation therapy by IMD 12 may include information identifying which electrodes have been selected for delivery of pulses according to the program, and the polarities of the selected electrodes, i.e., the electrode configuration for the program. In addition, a therapy parameter may include the particular pattern and/or locations of anodes and cathodes of the electrodes of leads 16 (the "electrode combination"). Programs that control delivery of other therapies by IMD 12 may include other parameters. For example, a program that controls delivery of a drug or other therapeutic agent may include a titration rate or information controlling the timing (e.g., frequency) of bolus deliveries.

In exemplary embodiments, IMD 12 stores the therapy programs as a plurality of records that are stored in a table or other data structure that may be continually updated as IMD 12 "learns" associations of therapy information with patient parameter values. Techniques for generating and updating the records within the table or other data structure are described in commonly-assigned U.S. Patent Application Publication No. 2007/0129774 by Bourget et al., entitled, "CLOSED-LOOP THERAPY ADJUSTMENT" and filed on Apr. 28, 2006, commonly-assigned U.S. Patent Application Publication No. 2007/0150029 by Bourget et al., entitled, "CLOSED-LOOP THERAPY ADJUSTMENT" and filed on Dec. 1, 2006, and commonly-assigned U.S. Patent Application Publication No. 2007/0150026 by Bourget et al., entitled, "CLOSED-LOOP THERAPY ADJUSTMENT" and filed on Dec. 1, 2006, each of which is incorporated herein by reference in its entirety. While the remainder of the disclosure refers primarily to tables, the present disclosure also applies to other types of data structures that store therapy programs and associated physiological parameters.

As described below with reference to FIG. 5, each record within a table stored within IMD 12 includes at least one patient parameter value and associated therapy information. The therapy information may define one or more therapy parameter values, absolute or percentage adjustments for one or more therapy parameters or a complete therapy program that IMD 12 implements to deliver therapy to patient 14. As described in further detail below, when IMD 12 detects a value of a patient parameter, IMD 12 may adjust the therapy delivery based on the therapy information in the records of the table. For example, upon determining a patient parameter value, IMD 12 may locate the record in the stored table including the patient parameter value and deliver therapy according to the therapy program associated with the patient parameter value. Alternatively, IMD 12 may interpolate between two therapy programs if the table does not include any records that associate the particular patient parameter value with a therapy program. As described in further detail below, the rate at which IMD 12 adjusts therapy delivery between two or more therapy programs may be determined based on a rate of change of one or more patient parameter values, such as a rate of change between the patient parameter values with which the programs are associated.

In the illustrated example, system 10 also includes a programming device 20, which may, as shown in FIG. 1, be a handheld computing device. Programming device 20 allows a user to interact with IMD 12. Programming device 20 may, for example, communicate via wireless communication with IMD 12 using radio-frequency (RF) telemetry techniques, or any other techniques known in the art. Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude.

In some embodiments, programming device 20 is a patient programmer used by patient 14 to control the delivery of neurostimulation therapy by IMD 12. Patient 14 may use programming device 20 to activate or deactivate, e.g., start or stop, neurostimulation therapy. Patient 14 may also use programming device 20 to adjust the therapy. For example, when IMD 12 is in one mode, a patient may use programming device 20 to manually select one or more programs from among a plurality of stored programs to be the current programs used by IMD 12 to deliver therapy, e.g., patient 14 may switch from one program to another using programming device 20. Further, patient 14 may also use programming device 20 to adjust therapy by adjusting one or more stimulation parameters, e.g., adjust the amplitude, width, or rate of delivered stimulation pulse, for the one or more current programs. However, as described herein, in another mode, IMD 12 is programmed to automatically select a therapy program from a plurality of stored programs or interpolate between the stored programs based on a sensed patient parameter value.

In some embodiments, the table of therapy programs and associated patient parameter values may be maintained by and/or stored within programming device 20 instead of IMD 12. Accordingly, one or both of IMD 12 and programming device 20 may provide closed-loop adjustment of the therapy delivered by IMD 12. In embodiments in which programming device 20 maintains the table, programming device 20 may include sensors that sense the patient parameter, or may receive values of the patient parameter from IMD 12 or another implanted or external sensor. After selecting a program or generating an intermediate program by interpolating between the therapy parameters of two therapy programs based on a sensed patient parameter value, programming device 20 may send commands to IMD 12 based on therapy information stored in the table to implement closed-loop delivery of therapy.

For ease of description, the provision of closed-loop therapy adjustment will be described hereinafter primarily with reference to embodiments in which IMD 12 provides the closed-loop therapy adjustments. However, it is understood that both of IMD 12 and programming device 20 are medical devices capable of providing closed-loop therapy adjustments according to the techniques described in the disclosure.

Figure 2:
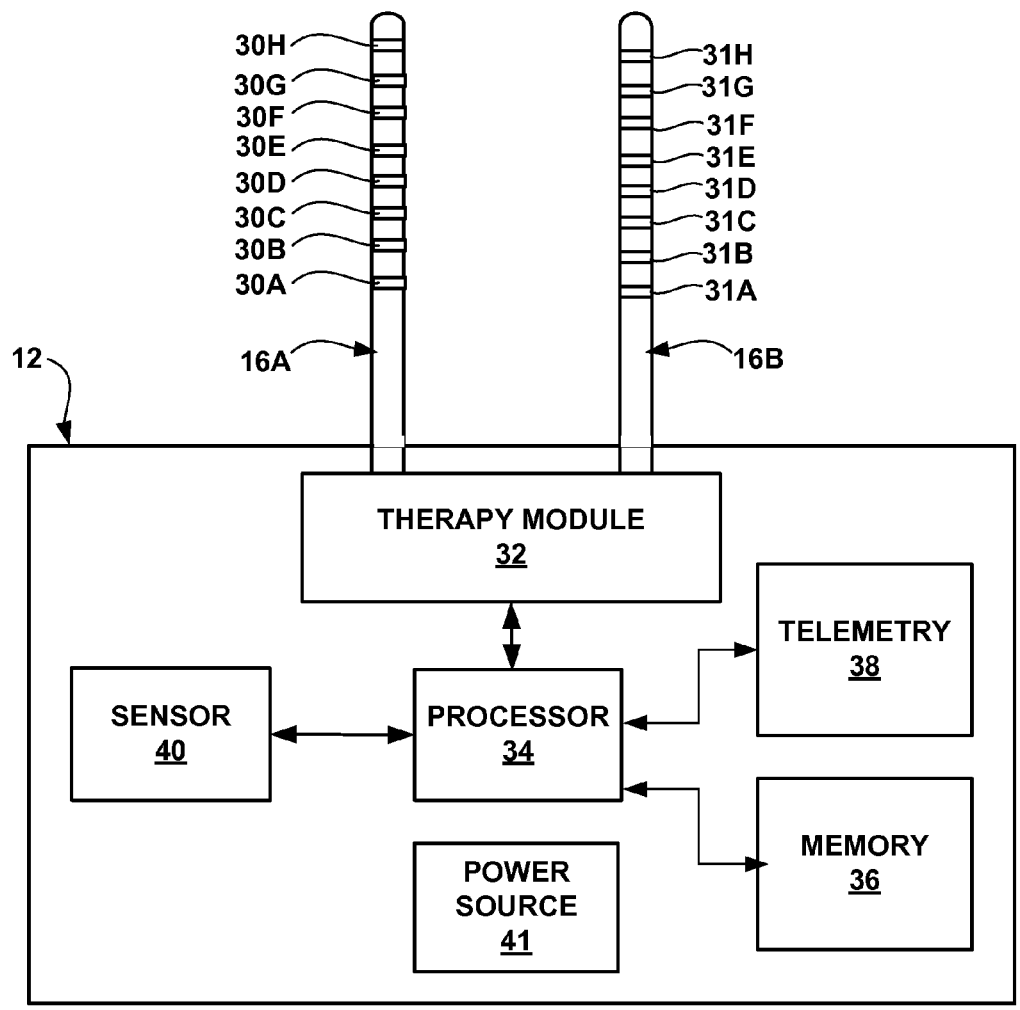
FIG. 2 is a block diagram illustrating the implantable medical device of FIG. 1 in greater detail.

FIG. 2 is a block diagram illustrating IMD 12 in greater detail. IMD 12 is coupled to leads 16A, 16B, which include electrodes 30A-H and 31A-H, respectively. IMD 12 may be coupled to leads 16A, 16B either directly or indirectly via a lead extension. IMD 12 includes therapy module 32, processor 34, memory 36, telemetry module 38, sensor 40, and power source 41.

IMD 12 may deliver neurostimulation therapy via electrodes 30A-H of lead 16A and electrodes 31A-H of lead 16B (collectively "electrodes 30 and 31"). In the embodiment shown in FIG. 2, implantable medical leads 16A and 16B are cylindrical. In other embodiments, leads 16A and 16B may be, at least in part, paddle-shaped (i.e., a "paddle" lead). In some embodiments, electrodes 30, 31 may be ring electrodes. In other embodiments, electrodes 30, 31 may be segmented or partial ring electrodes, each of which extends along an arc less than 360 degrees (e.g., 90-120 degrees) around the outer perimeter of the respective lead 16A, 16B. The configuration, type, and number of electrodes 30, 31 illustrated in FIG. 2 are merely exemplary. For example, IMD 12 may be coupled to one lead with eight electrodes on the lead or to three leads with the aid of a bifurcated lead extension.

Electrodes 30, 31 are electrically coupled to a therapy module 32 of IMD 12 via conductors within the respective leads 16A, 16B. Each of electrodes 30, 31 may be coupled to separate conductors so that electrodes 30, 31 may be individually selected, or in some embodiments, two or more electrodes 30 and/or two or more electrodes 31 may be coupled to a common conductor. In one embodiment, an implantable signal generator or other stimulation circuitry within therapy module 32 delivers electrical signals (e.g., pulses or substantially continuous-time signals, such as sinusoidal signals) to a target tissue site within patient 14 via at least some of electrodes 30, 31 under the control of processor 34. The stimulation energy generated by therapy module 32 may be delivered from therapy module 32 to selected electrodes 30, 31 via a switch matrix and conductors carried by leads 16, as controlled by processor 34.

Processor 34 may include any one or more of a microprocessor, a controller, a digital signal processor (DSP), an application specific integrated circuit (ASIC), a field programmable gate array (FPGA), discrete logic circuitry, or the like. Processor 34 controls the implantable signal generator within therapy module 32 to deliver electrical stimulation therapy according to selected therapy parameters. Specifically, processor 34 controls therapy module 32 to deliver electrical signals with selected voltage or current amplitudes, pulse widths (if applicable), and rates specified by the stimulation parameters (i.e., therapy parameters). The therapy parameters may be defined as part of a therapy program. In addition, processor 34 may also control therapy module 32 to deliver the electrical stimulation signals via selected subsets of electrodes 30, 31 with selected polarities. For example, electrodes 30, 31 may be combined in various bipolar or multi-polar combinations to deliver stimulation energy to selected sites, such as nerve sites adjacent the spinal column, pelvic floor nerve sites or cranial nerve sites. The above-mentioned switch matrix may be controlled by processor 34 to configure electrodes 30, 31 in accordance with a therapy program.

IMD 12 also includes a memory 36, which may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 36 may store program instructions that, when executed by processor 34, cause IMD 12 to perform the functions ascribed to IMD 12 herein. Memory 36 may also store a table of therapy programs (e.g., the therapy parameters of each therapy program) and associated patient parameter values.

In some embodiments, processor 34 maintains, e.g., creates and modifies, the table stored in memory 36. For example, in some embodiments, processor 34 maintains the table in accordance with the techniques described in commonly-assigned U.S. Patent Application Publication No. 2007/0129774 by Bourget et al., entitled, "CLOSED-LOOP THERAPY ADJUSTMENT" and filed on Apr. 28, 2006, commonly-assigned U.S. Patent Application Publication No. 2007/0150029 by Bourget et al., entitled, "CLOSED-LOOP THERAPY ADJUSTMENT" and filed on Dec. 1, 2006, and U.S. Patent Application Publication No. 2007/0150026 by Bourget et al., entitled, "CLOSED-LOOP THERAPY ADJUSTMENT" and filed on Dec. 1, 2006.

IMD 12 includes a sensor 40 that senses one or more patient parameters. Processor 34 detects values of the patient parameter based on the signal generated by sensor 40 as a function of the patient parameter. Sensor 40 may be a sensor that generates an output, such as an electrical signal, based on activity, activity level, posture, and/or one or more physiological parameters of patient 14, as discussed above. In some embodiments, processor 34 receive the electrical signal from sensor and determines a parameter value from the signal. In exemplary embodiments, sensor 40 is a 3-axis accelerometer, such as a piezoelectric and/or micro-electro-mechanical accelerometer. In other embodiments, a single axis accelerometer may be employed, or multiple single axis accelerometers may be used in place of one 3-axis accelerometer.

In some embodiments, processor 34 processes the analog output of sensor 40 to determine digital activity and/or posture information. For example, where sensor 40 comprises a piezoelectric accelerometer, processor 34 may process the raw signal provided by sensor 40 to determine activity counts, whereby the table of therapy information stored within memory 36 associates a therapy program with a number of activity counts. In some embodiments, IMD 12 includes one or more sensors oriented along various axes, or sensor 40 comprises a single multi-axis, e.g., three-axis, accelerometer. In such embodiments, processor 34 may process the signals provided by the one or more sensors 40 to determine velocity of motion information for each axis.

In other embodiments, IMD 12 may include an ultrasonic transducer on at least one of leads 16A, 16B to detect movement relative to a target tissue site. An example of a technique for detecting relative movement between a target tissue site and at least one of leads 16A, 16B is provided in commonly-assigned U.S. Pat. No. 7,406,351 to Wesselink et al., entitled, "ACTIVITY SENSING FOR STIMULATOR CONTROL," and issued on Jul. 29, 2008. As previously described, the movement of leads 16A, 16B within patient 14 may affect the efficacy of therapy, for example, by changing the intensity of stimulation perceived by patient 14. Accordingly, a position of leads 16A, 16B relative to a target tissue site may represent a patient parameter value that may be associated with a therapy program. Upon detecting lead 16A, 16B movement relative to the target tissue site, a therapy program may be adjusted.

Although illustrated in FIG. 2 as including a single sensor 40, systems according to the disclosure may include any number of sensors 40. In exemplary embodiments, the one or more sensors 40 are housed within a housing (not shown) of IMD 12. However, the disclosure is not so limited. In some embodiments, one or more sensors 40 are coupled to IMD 12 via additional leads 16 (not shown). Such sensors may be located anywhere within patient 14. In some embodiments, IMD 12 may be coupled to multiple accelerometer sensors 40 located at various positions within patient 14 or on the external surface of patient 14, and processor 34 may receive more detailed information about the posture of and activity undertaken by patient 14. For example, accelerometer sensors 40 may be located within the torso and at a position within a limb, e.g. a leg, of patient 14.

In some embodiments, one or more sensors 40 may communicate wirelessly with IMD 12 instead of requiring a lead to communicate with the IMD. For example, sensors 40 located external to patient 14 or implanted separately from IMD 12 may communicate wirelessly with processor 34, either directly or via programming device 20. In some embodiments, one or more sensors 40 may be included as part of or coupled to programming device 20.

Moreover, the disclosure is not limited to embodiments where sensors 40 are accelerometers. In some embodiments, one or more sensors 40 may take the form of, for example, a thermistor, a pressure transducer, or electrodes to detect thoracic impedance or an electrogram. Such sensors 40 may be appropriately positioned within patient 14, or on an external surface of the patient, to allow processor 34 to measure a physiological parameter of patient 14, such as a skin temperature, an arterial or intracardiac pressure, a respiration rate, a heart rate, or a Q-T interval of patient 14.

Processor 34 may also control therapy module 32 to deliver the electrical stimulation to patient 14 according to records stored within a table stored in memory 36, as described above. In particular, processor 34 may monitor the patient parameter via sensor 40 and select a therapy program that is associated with the sensed patient parameter from the stored table. A range of patient parameters may be associated with a single therapy program because patient 14 may find the therapy program effective for multiple patient conditions represented by the range of patient parameters.

Processor 34 may transition between therapy programs based on the rate of change in the sensed patient parameter in order to provide a gradual change to minimize any discomfort to patient 14. For example, if sensor 40 is configured to generate a signal indicative of a posture of patient 14, and processor 34 determines, based on the signal from sensor 40, that patient 14 is moving from a recumbent posture to a standing posture, processor 34 may control therapy module 32 to transition therapy delivery from a program associated with the recumbent posture to a program associated with the sitting posture prior to delivering therapy according to a program associated with the standing posture based on the detected rate of movement between the recumbent and standing postures. Processor 34 may determine the rate of movement based on the trend in signals received from sensor 40. The trend may be, for example, the rate of change of the signal over time, which indicates the rates of change in the sensed patient parameter that is indicative of posture over time.

Depending upon the differences in the therapy parameters of the first and second programs, patient 14 may notice the shift in therapy from the first program to the second program. For example, if the first program is associated with a recumbent posture, while the second program is associated with a standing posture, an amplitude of stimulation therapy may be greater for the second program. Accordingly, patient 14 may notice an abrupt change in the stimulation therapy from therapy according to the first program to therapy according to the second program. Gradually transitioning between the first and second therapy programs at a rate that is determined based on the patient's movement between the two postures may minimize any noticeable change in therapy to patient 14.

In the embodiment in which patient 14 changes posture from a recumbent posture to a standing posture, if the sensed patient parameter value associated with the standing posture is present in the table stored within memory 36, processor 34 may select the therapy program associated with the standing posture and begin delivering therapy according to the selected therapy program. However, as described above, it may be desirable to gradually transition between the therapy programs associated with the recumbent and standing postures. Thus, processor 34 may implement one or more intermediate therapy programs as processor 34 shifts between the therapy programs associated with the recumbent and standing postures. The intermediate therapy program may be associated with, for example, a sitting posture, which may be a posture between the recumbent and standing postures. Alternatively, processor 34 may generate the intermediate therapy program that is based on the therapy programs within the table of programs stored in memory 36 using one of the techniques described below. The recumbent and standing postures are used herein merely as examples. In other embodiments, processor 34 may transition between therapy programs associated with other patient postures or other patient parameters.

If the sensed patient parameter is not present in the table or within a certain range of a parameter value in the table, and, thus, not associated with any stored therapy program, processor 34 may interpolate between two programs in the table. In one embodiment, IMD 12 may reference the table stored in memory 36 to determine whether to interpolate between two predetermined therapy programs, and to select the programs to interpolate between. For example, if therapy delivery module 32 is delivering therapy according to a first program, but processor 34 determines that the sensed patient parameter has changed and is no longer associated with the first program, processor 34 may reference the table to determine what program, if any, is associated with the current value of the sensed physiological parameter. Because the table includes discrete parameter values associated with discrete programs, processor 34 may select the most closely related program (e.g., the program associated with a parameter value that is the closest to the current patient parameter value out of all the parameter values in the table) and deliver therapy according to the most closely related program. However, the most closely related program may not be the most optimal for the patient's current posture or activity level.

According to some techniques of the present disclosure, processor 34 may identify the most closely related program, but rather than delivering therapy according to that program, processor 34 may implement an algorithm to interpolate between the current therapy parameters and the therapy parameters of the most closely related program. The algorithm may, for example, set forth maximum increments in a particular therapy parameter value, such as increases in the amplitude of electrical stimulation.

In some embodiments, processor 34 may only interpolate between a current therapy program and a next closest program based if the sensed patient parameter value not only is not associated with a therapy program, but differs from any of the physiological parameter values in the table by a threshold value, which may be for example an absolute or percentage value. The threshold value may be set by, for example, a manufacturer of IMD 12 or a clinician, and controls difference in the parameter value that processor 34 identifies as being significant enough to interpolate between two therapy programs. If the threshold value is set to a low value, processor 34 may interpolate between the current therapy program and the therapy program that is associated with a patient parameter value that is closest to the currently sensed patient physiological parameter value. Alternatively, the threshold value may be set to a higher value to minimize the frequency with which processor 34 interpolates between two therapy programs.

Processor 34 may monitor the signal from sensor 40 at regular intervals or substantially continuously in order to determine whether to change the therapy program by which therapy module 32 delivers electrical stimulation therapy to patient 14. In this way, signals from sensor 40 are used in a closed-loop therapy program adjustment technique implemented by processor 34. In other embodiments, a separate processor, rather than processor 34 of IMD 12 may be used to monitor the signal from sensor 40 and select therapy programs for implementation based on the sensed patient parameter or interpolate between two therapy programs. IMD 12 may include another processor or the separate processor may be included within a separate medical device (either implanted within patient 14 or carried external to patient 14). The separate processor may provide an input to processor 34 that indicates the sensor output or the input to processor 34 may indicate processor 34 should implement a change in therapy program based on the change in the sensor 40 output. In addition, in some embodiments, the separate processor may also determine a rate of change between adjusting therapy delivery between two or more therapy programs and/or interpolate between therapy parameters of two or more programs. Use of a processor separate from processor 34, and especially a separate processor in another medical device, may help conserve power source 41 and extend the useful life of IMD 12.

IMD 12 also includes a telemetry circuit 38 that allows processor 34 to communicate with programming device 20. Processor 34 may receive program selections, therapy parameter adjustments, or other therapy adjustments that override the therapy program selected by processor 34, as well as commands to initiate or terminate stimulation, from a user, e.g., patient 14, using programming device 20 via telemetry circuit 38. In some embodiments, as will be described in greater detail below, processor 34 also communicates with a clinician programmer to provide diagnostic information stored in memory 36 to a clinician via telemetry circuit 38. The diagnostic information may be, for example, the patient parameter values detected by sensor 40. The clinician programmer may operate similarly to programmer 20, but the clinician programmer may be more fully featured, e.g., provide greater control of or interaction with IMD 12, than programming device 20. Telemetry circuit 38 may correspond to any telemetry circuit known in the implantable medical device arts.

Therapy module 32 and processor 34 may be coupled to power source 41. Power source 41 may take the form of a small, rechargeable or non-rechargeable battery, or an inductive power interface that transcutaneously receives inductively coupled energy. In the case of a rechargeable battery, power source 41 similarly may include an inductive power interface for transcutaneous transfer of recharge power.

Figure 3:
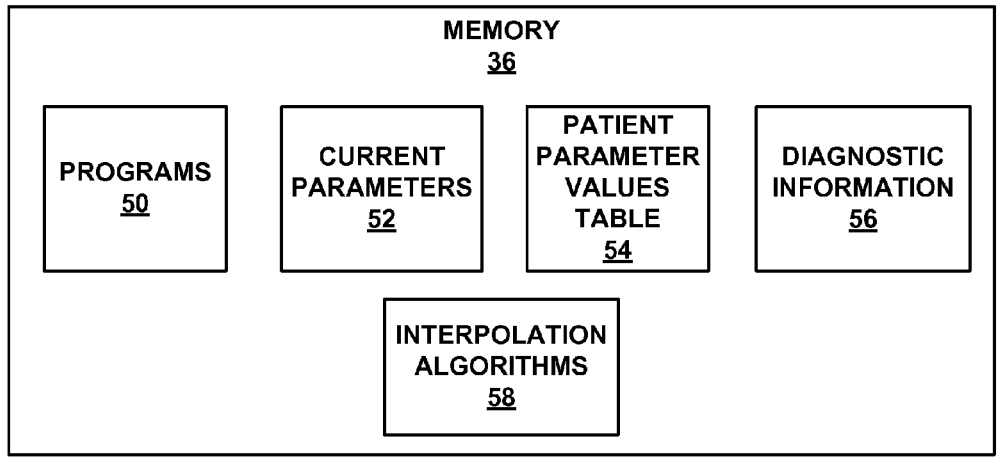
FIG. 3 is a block diagram illustrating an exemplary configuration of a memory of the implantable medical device of FIG. 2.

FIG. 3 is a block diagram illustrating an example configuration of memory 36 of IMD 12. As illustrated in FIG. 3, memory 36 stores therapy programs 50, one or more of which processor 34 (FIG. 2) may select to control delivery of stimulation by therapy module 32 (FIG. 2), as described above. Each of the programs includes respective values for a plurality of therapy parameters, such as pulse amplitude, pulse width, pulse rate, and electrode configuration. Processor 34 may select one or more programs based on a patient parameter value, which may be determined based on input from sensor 40. Programs 50 may have been generated using a clinician programmer, e.g., during an initial or follow-up programming session, and received by processor 34 from the clinician programmer via telemetry circuitry 38. In other embodiments, programming device 20 stores programs 50, and processor 34 receives selected programs from programming device 20 via telemetry circuit 38.

In some embodiments, memory 36 also stores an indication of the current therapy parameters 52 used by processor 34 to control delivery of stimulation by therapy module 32. Current therapy parameters 52 may be the one or more selected programs, or may reflect modifications to one or more therapy parameters of the one or more programs based on an interpolation between two or more stored programs 50. Further, processor 34 may determine current therapy parameters 52 based on therapy information associated with a detected value of a sensed patient parameter, which is determined via sensor 40.

As described above, patient parameter values table 54 comprises a plurality of records that each include a respective value of a patient parameter and associated therapy information. Processor 34 may also collect diagnostic information 56 and store diagnostic information 56 within memory 36 for future retrieval by a clinician. Diagnostic information 56 may, for example, include selected recordings of the output of sensor 40. In exemplary embodiments, diagnostic information 56 includes information identifying the time at which patient sensor outputs occurred, either during operation in a learning mode or as subsequently detected by processor 34. Diagnostic information 56 may include other information or activities indicated by patient 14 using programming device 20, such as changes in symptoms, medication ingestion or other activities undertaken by patient 14. A clinician programming device (not shown in FIGS.) may present diagnostic information 56 to a clinician in a variety of forms, such as timing diagrams, or a graph resulting from statistical analysis of diagnostic information 56, e.g., a bar graph. Diagnostic information 56 may also include calibration routines for each sensor 40 and malfunction algorithms to identify stimulation dysfunctions. Memory 36 may also store interpolation algorithms 58, which include algorithms employed by processor 34 to interpolate one or more therapy parameter values between two therapy programs stored within programs 50. The algorithms in interpolation algorithms 58 may include both linear and nonlinear algorithms.

Figure 4:
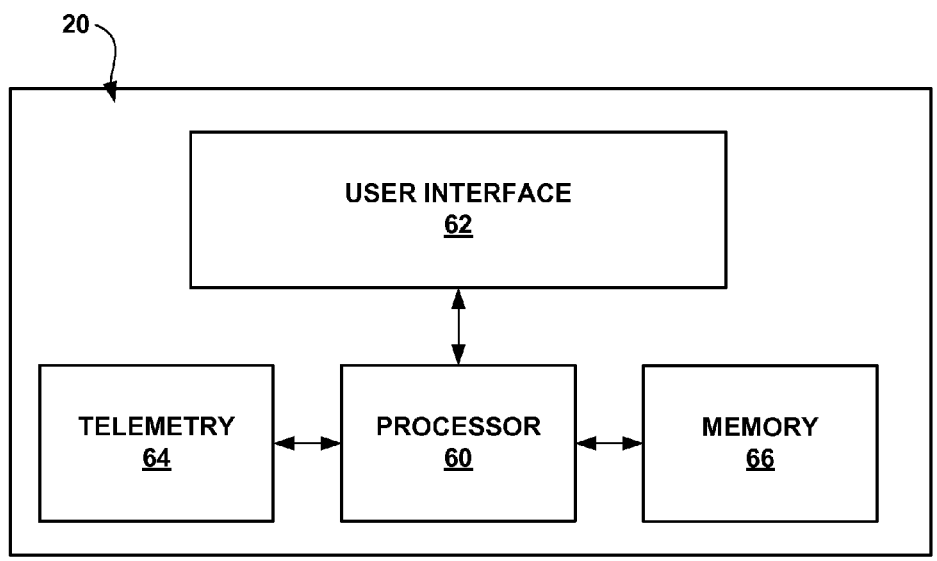
FIG. 4 is a block diagram of one embodiment of the programming device of the system shown in FIG. 1.

FIG. 4 is a block diagram further illustrating programming device 20. As indicated above, in exemplary embodiments programming device 20 may take the form of a patient programming device used by patient 14 or a clinician programming device used by a clinician. Patient 14 or the clinician may interact with a processor 60 via a user interface 62 in order to control delivery of electrical stimulation therapy, e.g., provide therapy adjustments, if desired. User interface 62 may include display 22 and keypad 24, and may also include a touch screen or peripheral pointing devices as described above. Keypad 24 may include an increase amplitude button and a decrease amplitude button. Processor 60 may also provide a graphical user interface (GUI) to facilitate interaction with patient 14. Processor 60 may include a microprocessor, a controller, a DSP, an ASIC, an FPGA, discrete logic circuitry, or the like.

Programming device 20 also includes a telemetry circuit 64 that allows processor 60 to communicate with IMD 12. In exemplary embodiments, processor 60 communicates commands, indications, and therapy adjustments made by patient 14 via user interface 62 to IMD 12 via telemetry circuit 64. Telemetry circuit 64 may correspond to any telemetry circuit known in the implantable medical device arts.

Programming device also includes a memory 66. In some embodiments, memory 66, rather than memory 36 of IMD 12, may store programs 50 and table 54 to control delivery of electrical stimulation therapy. Memory 66 may also include program instructions that, when executed by processor 60, cause programming device 20 to perform the functions ascribed to programming device 20 herein. Memory 66 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 5:
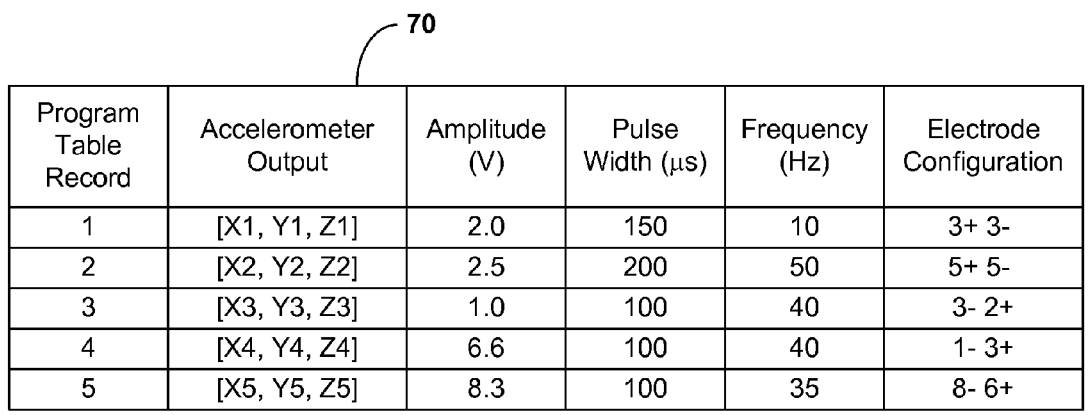
FIG. 5 illustrates an example patient parameter value table that may be used for closed-loop adjustment of therapy.

FIG. 5 illustrates an example patient parameter value table 70 that may be used for closed-loop adjustment of therapy. Table 70 may correspond to table 54 (FIG. 3) stored in memory 36 of IMD 12. As shown in FIG. 5, table 70 includes a plurality of records. Each record contains a 3-axis accelerometer output, which is an example of a value of a sensed patient parameter, as well as an associated therapy program. In the embodiment shown in FIG. 5, the therapy parameters of each therapy program are shown in table 70, and include an amplitude, a pulse width, a pulse frequency, and an electrode configuration. Processor 34 may search table 70 based on a currently-detected accelerometer output in order to match therapy to the current condition, e.g., posture, of patient 14.

Sensor 40 (FIG. 2) of IMD 12 may include the 3-axis accelerometer, whose output may indicate a patient posture. A measured acceleration in each direction creates a vector acceleration. Therefore, each accelerometer output includes an X variable, a Y variable, and a Z variable. The value of the accelerometer may be a raw value or a calibrated value equal to the actual acceleration. The resolution value may be equal to the maximum range of each acceleration component divided by a pre-set size. For example, the maximum range may be 10 volts, and the pre-set size may be 100. Therefore, the resolution value for each component is 0.1 volts. In some embodiments, each component of the acceleration value may have a different resolution value.

With respect to the therapy information, the amplitude is in volts, the pulse width is in microseconds (µs), the pulse frequency is in Hertz (Hz), and the electrode configuration determines the electrodes and polarity used for delivery of stimulation according to the record. The amplitude of program table 70 is the voltage amplitude, but other embodiments may use a current amplitude. In the illustrated example, each record includes a complete set of therapy parameters, e.g., a complete program, as therapy information. In other embodiments, each record may include one or more individual parameter values, or information characterizing an adjustment to one or more parameter values.

When processor 34 detects an output from the accelerometer, e.g., when patient 14 is in a recumbent posture, processor 34 may automatically deliver therapy appropriate for the recumbent posture by selecting therapy program in the table 70 that is associated with an accelerometer output that substantially matches or is within a predetermined range of the detected accelerometer output. The predetermined range may be determined by the clinician or another user, and in some embodiments, may be customized to patient 14. By providing therapy adjustments automatically, IMD 12 provides closed-loop control of the therapy parameters, which may allow patient 14 to avoid having to manually adjust the therapy each time a particular patient parameter value occurs, e.g., each time the patient engages in a particular activity, activity level or posture. Such manual adjustment of stimulation parameters can be tedious, requiring patient 14 to, for example, depress one or more keys of keypad 24 of programming device 20 (FIG. 1) multiple times during the patient activity to maintain adequate symptom control.

The look-up table 70, however, is limited in breadth of coverage for all patient postures because, for example, of limits in the capacity of memory 36. Thus, in some cases, processor 34 may detect an output from the accelerometer that is not present in table 70 or within a predetermined range of an accelerometer output that is present in table 70. In such cases, processor 34 may interpolate between two programs in table 70 to generate a therapy program that best-suits the detected accelerometer output.

Figure 6:
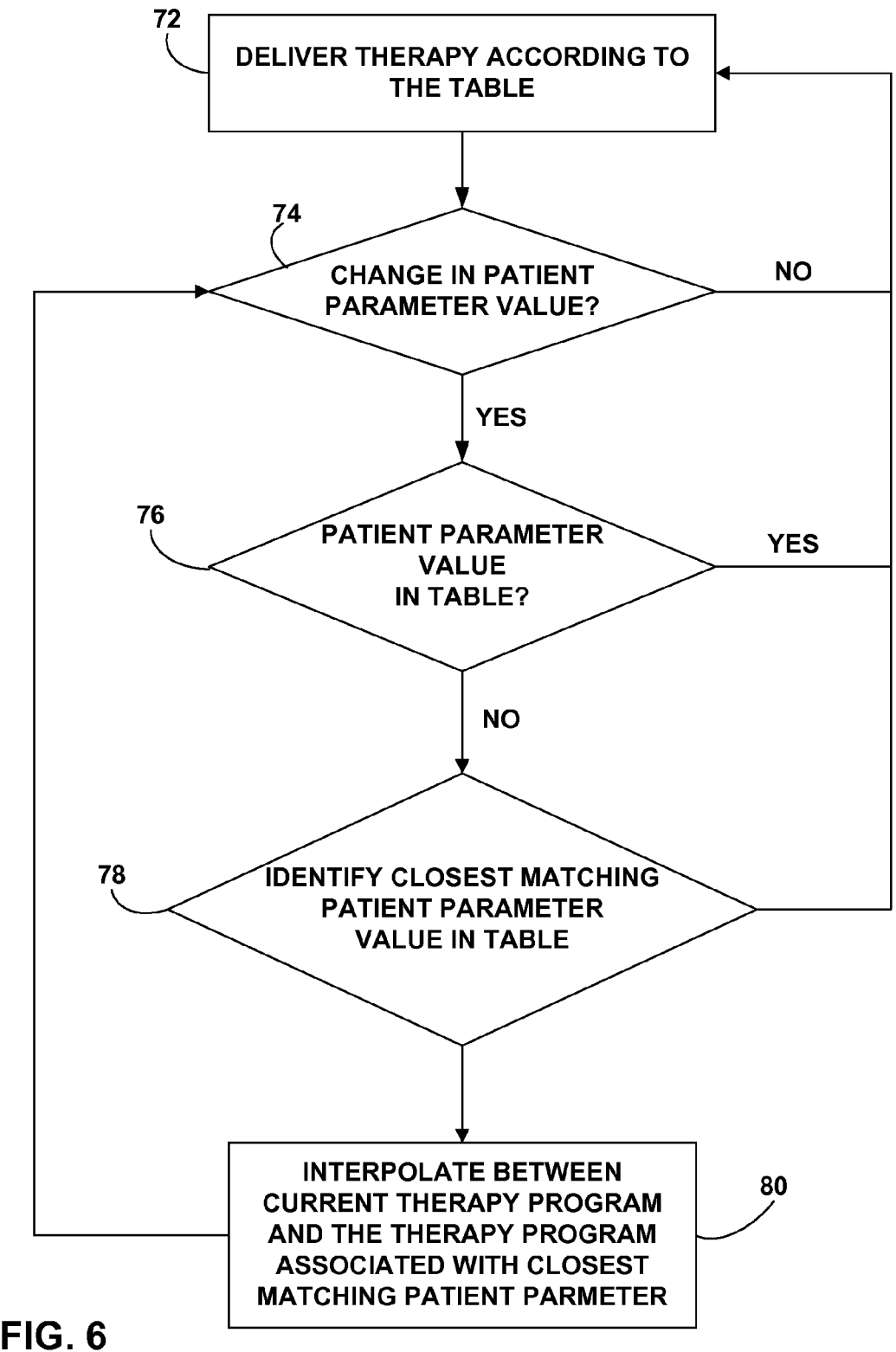
FIG. 6 is a flow chart illustrating an example of a technique that a processor of an implantable medical device may employ to interpolate between two therapy programs.

An example of a technique that processor 34 may employ to interpolate between two therapy programs is shown in the flow diagram of FIG. 6. Processor 34 may control therapy module 32 (FIG. 2) to deliver therapy according to a therapy program within table 70 (72). For example, as described above, patient 14 may be in a recumbent posture, and processor 34 may select a therapy program for implementation by therapy module 32 from table 70, where the therapy program is associated with an accelerometer output indicative of the recumbent posture. Processor 34 may monitor the signal from sensor 40 (FIG. 2) to detect a change in the patient parameter value, i.e., in this example, a change in the accelerometer output that indicates a change in patient posture (74). While the remainder of the description of FIG. 6 refers to accelerometer output, in other embodiments, other patient parameter values may be monitored by other types of sensors 40 and table 70 may associate other types of patient parameter values with therapy programs.

In one embodiment, processor 34 may compare a first accelerometer output signal with a second accelerometer output signal that was generated by the accelerometer after the first signal in order to determine whether the patient posture changed. In another embodiment, processor 34 may determine whether there was a patient posture change based on the posture levels associated with the accelerometer signals, rather than merely comparing the first and second signals. In some cases, processor 34 may detect a posture change based on any output from an accelerometer or an accelerometer signal (e.g., an amplitude) that exceeds a certain threshold, because the accelerometer output typically indicates movement, and thus, may suggest patient movement. Other techniques for determining whether there was a change in patient posture based on the output of an accelerometer may be used.

If the signal from sensor 40 indicates there has not been a change in accelerometer output, therapy module 32 continues delivering therapy according to the therapy program associated with the accelerometer output in table 70 (72). If the signal from sensor 40 indicates the accelerometer output has changed, processor 34 may reference table 70 to determine whether the new accelerometer output is present in table 70 (76). The accelerometer output may indicate that a patient posture has changed, and that the currently implemented therapy program may not be as effective as other therapy programs. Thus, processor 34 may refer to table 70 to determine whether the new posture, as indicated by the accelerometer output, is associated with a stored therapy program. If the current accelerometer output is present in table 70, processor 34 selects the new therapy program and controls therapy module 32 to deliver therapy according to the therapy program associated with the current accelerometer output in table 70 (72).

If the new accelerometer output is not present in table 70, processor 34 finds the closest matching accelerometer output in table 70 in order to identify the closest matching therapy program (78) relative to the therapy program currently implemented by therapy module 32. Identifying the closest matching therapy program may help the processor 34 determine a range for therapy parameters of an interpolated program that may be effective for the patient's new posture. For example, referring to table 70 in FIG. 5, if the accelerometer output is [X1.5, Y1.5, Z1.5], which is midway between the accelerometer outputs [X1, Y1, Z1] and [X2, Y2, Z2] that are included in table 70, and the therapy program currently implemented by therapy module 32 is program 1 (shown in FIG. 5), processor 34 identifies accelerometer output [X2, Y2, Z2] as the closest matching patient parameter value. Alternatively, if the accelerometer output is [X1.5, Y1.5, Z1.5], and the therapy program currently implemented by therapy module 32 is program 2, processor 34 identifies accelerometer output [X1, Y1, Z1] as the closest matching patient parameter value.

After identifying the closest matching accelerometer output in table 70 and the associated therapy program (78), processor 34 may interpolate between the current therapy program and the program associated with the closest matching accelerometer output (80). Thus, in the example in which processor 34 identifies accelerometer output [X2, Y2, Z2] as the closest matching patient parameter value, processor 34 interpolates between therapy programs 1 and 2 to generate an intermediate therapy program that is best-suited to the new accelerometer output [X1.5, Y1.5, Z1.5] (80). Processor 34 may then control therapy module 32 to deliver therapy according to the interpolated intermediate therapy program. Processor 34 may continue to monitor the signal from sensor 40 to detect when the patient parameter changes (74), and adjust the therapy program or interpolate the therapy program as necessary to address the patient posture changes. In some cases, processor 34 may interpolate between an interpolated program and a stored therapy program, e.g., if the currently implemented therapy program is an interpolated program.

Therapy module 32 may deliver therapy according to an interpolated program during a transition between two programs within table 70 or instead of delivering therapy according to one of the stored programs of table 70. For example, the new accelerometer output [X1.5, Y1.5, Z1.5] may reflect that patient 14 is in the midst of changing postures between the posture associated with accelerometer output [X1, Y1, Z1] to the posture associated with accelerometer output [X2, Y2, Z2]. That is, because processor 34 monitors the accelerometer output at regular intervals or substantially continuously, processor 34 may determine an accelerometer output that reflects a patient posture that is incidental to movement between two patient postures. As one example, if accelerometer output [X1, Y1, Z1] is associated with a recumbent posture and accelerometer output [X2, Y2, Z2] is associated with a sitting posture, accelerometer output [X1.5, Y1.5, Z1.5] may be associated with a posture midway between a recumbent and sitting posture (e.g., a "reclined" posture). Accordingly, when processor 34 determines that the accelerometer output from sensor 40 is [X1.5, Y1.5, Z1.5], processor 34 may merely be detecting an accelerometer output that is the result of patient movement, not an actual posture that will be maintained by patient 14 for a significant amount of time (e.g., more than one minute). However, in order to provide a relatively smooth transition between the therapy program associated with the accelerometer output [X1, Y1, Z1] and [X2, Y2, Z2], processor 34 may interpolate an intermediate program that provides effective therapy to patient 14 for the intermediate posture associated with accelerometer output [X1.5, Y1.5, Z1.5]. In some cases, however, patient 14 may maintain the "intermediate" posture.

As another example of how therapy module 32 may deliver therapy according to an interpolated program during a transition between two programs stored within table 70, a change in accelerometer output to the output [X1.5, Y1.5, Z1.5] may suggest that patient 14 is in the midst of changing postures between the posture associated with accelerometer output [X1, Y1, Z1] to the posture associated with accelerometer output [X2, Y2, Z2]. However, subsequent accelerometer signals may indicate that patient 14 returned to the posture associated with accelerometer output [X1, Y1, Z1], rather than changing to the posture associated with accelerometer output [X2, Y2, Z2]. Accordingly, in that example, processor 34 may deliver therapy according to the interpolated program until processor 34 detects another accelerometer output change, e.g., the change indicating that patient 14 returned to the posture associated with accelerometer output [X1, Y1, Z1], at which time, processor 34 may reference table 70 and deliver therapy according to program 1, which is associated with the accelerometer output [X1, Y1, Z1]. The interpolated program may provide a better fit for the "intermediate" posture, in the sense that the posture is between two postures present in table 70. In some cases, delivery of therapy according to the interpolated program may provide a more efficient use of power in addition to a better fit, as compared to delivering therapy according to a program associated with a patient posture that patient 14 does not assume (in the example, program 2 associated with accelerometer output [X2, Y2, Z2]).

Figure 7A:
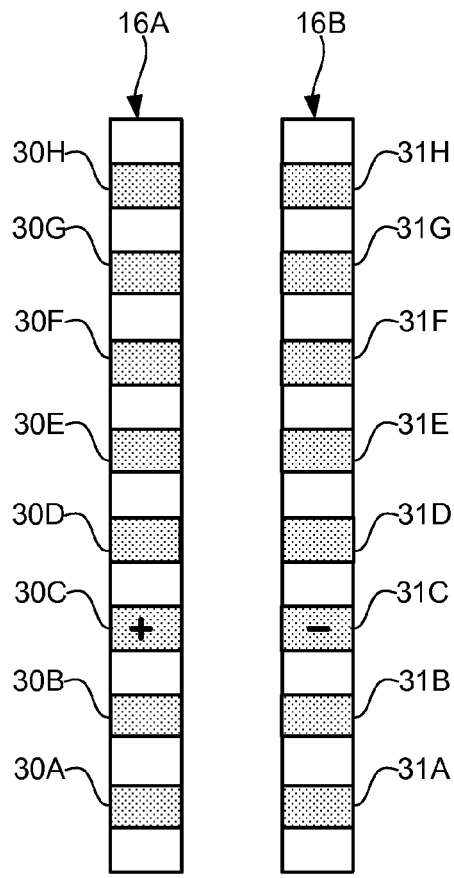
FIGS. 7A-7C illustrate an embodiment of a technique for interpolating an electrode combination between electrode combinations of two therapy programs.
Figure 7B:
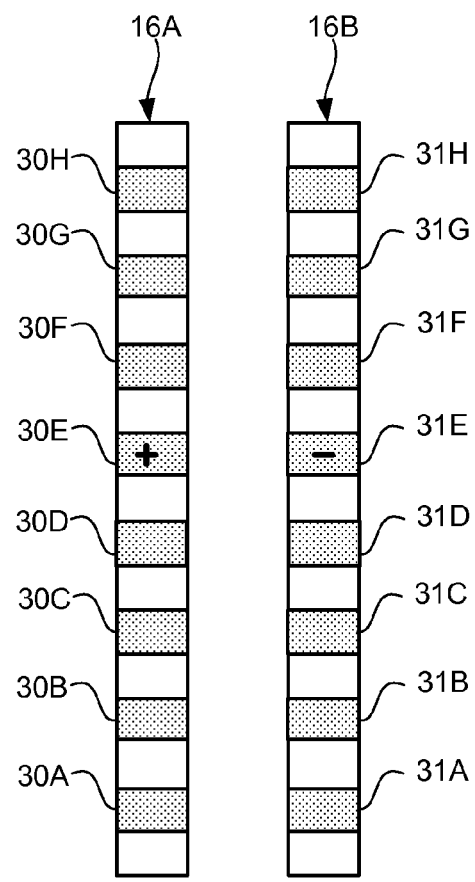
Figure 7C:
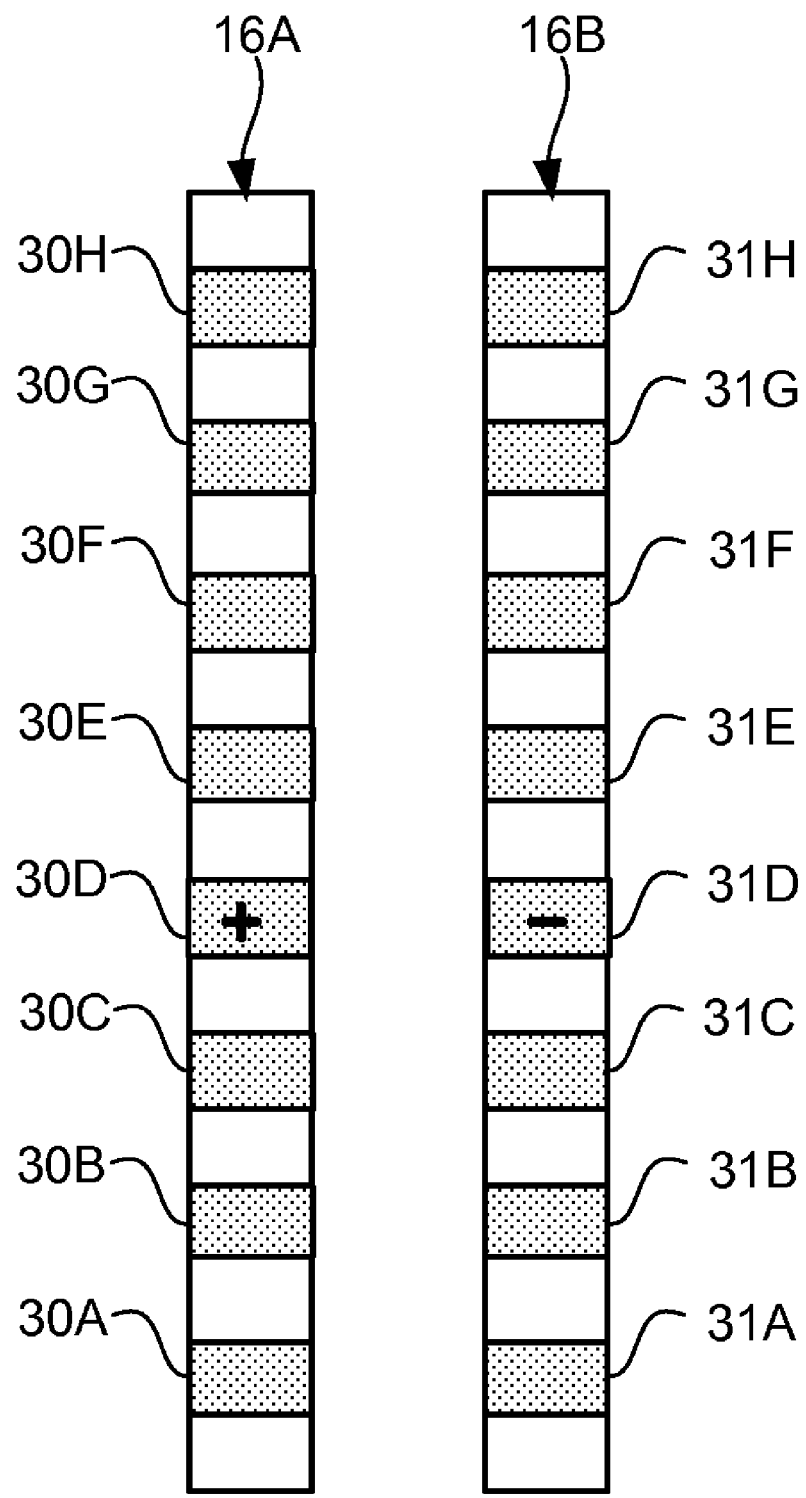

FIGS. 7A-7C illustrate an embodiment of a technique for interpolating between therapy programs 1 and 2 (shown in the table 70 of FIG. 5). FIG. 7A illustrates a first electrode combination on leads 16 (FIG. 2), which are coupled to therapy module 32. The electrode combination shown in FIG. 7A is a therapy parameter of therapy program 1, and the anode and cathode are both in the (3+, 3−) location, respectively, as indicated in table 70. In particular, electrode 30C of lead 16A is the anode and electrode 31C of lead 16B is the cathode of the electrode combination. As provided in table 70, therapy program 2 includes an electrode combination in which the anode and cathode are in the (5+, 5−) locations, respectively. As FIG. 7B illustrates, the electrode 30E of lead 16A is the anode and electrode 31E of lead 16B is the cathode in the electrode combination of therapy program 2.

In one embodiment, in order to interpolate between therapy programs 1 and 2, processor 34 implements an algorithm that determines an electrode combination that is intermediate to the electrode combinations of therapy program 1 (FIG. 7A) and therapy program 2 (FIG. 7B). As one example, processor 34 may implement an algorithm that linearly interpolates between the therapy parameters of therapy programs 1 and 2. As applied to the electrode combination therapy parameter, processor 34 may determine that the new accelerometer output [X1.5, Y1.5, Z1.5] is approximately halfway between the accelerometer outputs associated with therapy programs 1 and 2. Based on a linear interpolation technique, processor 34 may interpolate a program including an electrode combination approximately midway between the combinations shown in FIGS. 7A and 7B. FIG. 7C illustrates an example of an electrode combination that is approximately midway between the combinations of therapy programs 1 and 2. In particular, the interpolated program includes an electrode combination that includes an anode and cathode in a (4+, 4−) location, whereby electrode 30D of lead 16A is the anode and electrode 31D of lead 16B is the cathode.

As an example, processor 34 may use a table of possible electrode combinations arranged according to their axial positions on one or more leads may be used to identify an intermediate electrode combination for the purpose of interpolating between two programs. Such a table may be stored in memory 36. In some embodiments, a number of possible electrode combinations, including (4+, 4−), may be present in such a table between (3+, 3−) and (5+, 5−). Other possible combinations between (3+, 3−) and (5+, 5−) may include changes in the relative location or orientation of anodes and cathodes, e.g., (4−, 4+), and/or additional anodes and cathodes. In some cases, such a table may be generated, culled, or parsed based on user input and/or characteristics of the electrode combinations of programs 1 and 2. For example, in some embodiments, the selection of an intermediate electrode combination by processor 34 may be limited by the relative location or orientation of anodes and cathodes, or the number of electrodes or type of combination, e.g., bipole, guarded cathode, or tranverse tripole.

Processor 34 may implement a linear interpolation algorithm for determining the therapy parameters of the interpolated program other than the electrode combination. For example, in the embodiment in which the accelerometer output is [X1.5, Y1.5, Z1.5] and the therapy parameters include a frequency of electrical stimulation signals, as shown in table 70 (FIG. 5), processor 34 may select a frequency that is midway between the frequencies of therapy programs 1 and 2. With the example frequencies provided in table 70, processor 34 may select a frequency of about 30 Hz for the interpolated program.

In other embodiments, processor 34 may implement an algorithm that follows a nonlinear interpolation technique. For example, if patient 14 is afflicted with lower back pain that is intensified in a sitting position, and therapy program 1 is associated with a recumbent posture and therapy program 2 is associated with a sitting posture in which patient 14 feels a significant increase in pain as compared to the recumbent posture, the algorithm may consider the nonlinear increase in pain levels to interpolate between therapy programs 1 and 2. In one embodiment, rather than following a strictly linear interpolation in which processor 34 selects an electrode combination that is approximately midway between the combinations for therapies 1 and 2, processor 34 may implement a nonlinear algorithm and select the electrode combination associated with program 2 (shown in FIG. 7B). The nonlinear algorithm may reflect a consideration that although the patient posture indicated by the accelerometer output of [X1.5, Y1.5, Z1.5] is approximately midway between the accelerometer outputs associated with therapy programs 1 and 2, the pain level associated with the patient posture is likely to be more than half the pain treated by program 2. Similar nonlinear interpolation techniques may be employed for determining the other therapy parameters of an interpolated program, such as the amplitude, pulse width, and frequency of electrical stimulation.

Processor 34 may also implement a linear interpolation algorithm or a nonlinear interpolation algorithm to determine the therapy parameters, such as voltage or current amplitude, pulse width or pulse frequency of electrical stimulation, for the intermediate program. The shifting of stimulation energy between two programs, e.g., between the electrode combinations of FIGS. 7A and 7C may be implemented via any suitable technique. In one embodiment, processor 34 provides instructions that cause therapy module 32 to time-interleave stimulation energy between the electrode combinations of FIGS. 7A and 7C, as described in commonly-assigned U.S. Pat. No. 7,519,431 to Steven Goetz et al., entitled, "SHIFTING BETWEEN ELECTRODE COMBINATIONS IN ELECTRICAL STIMULATION DEVICE," and issued on Apr. 14, 2009, the entire content of which is incorporated herein by reference. In the time-interleave shifting embodiment, the amplitudes of the first and second electrode combinations (FIGS. 7A and 7C, respectively) are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off.

In another embodiment, shifting electrical stimulation and in particular, the current, between two electrode combinations of respective therapy programs is achieved by reducing an amplitude delivered to an electrode of one combination relative to the increase in amplitude an electrode of another combination. In such embodiments, therapy module 32 (FIG. 2) may include at least two current sources. For example, to shift between therapy program 1 (FIG. 7A) and an interpolated therapy program (FIG. 7C), the amplitude of current provided to electrode 30C on lead 16A may be reduced as the amplitude of current provided to electrode 30D on lead 16A is increased. The reduction in amplitude of current provided to electrode 30C may be proportionate to the increase in amplitude of current provided to electrode 30D. It may be desirable to maintain the current at a relatively consistent perceptual intensity for patient 14 in order to prevent the current from exceeding a maximum threshold for patient 14, above which, patient 14 may feel pain or discomfort.

Figure 8:
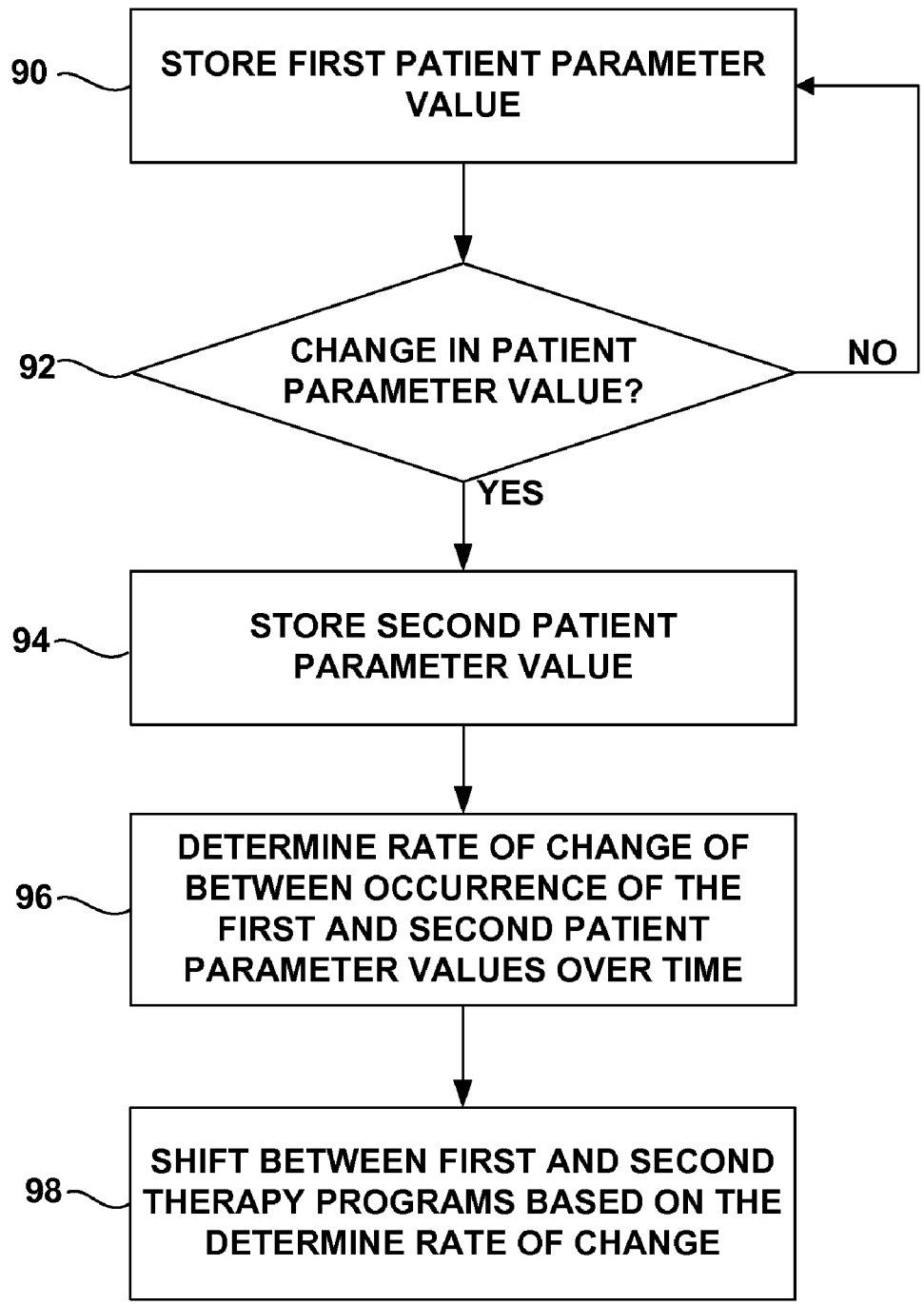
FIG. 8 is a flow diagram illustrating an embodiment of a technique for determining a rate for adjusting therapy delivery between the therapy parameters of two therapy programs.

The rate of shifting between two therapy programs, whether the two therapy programs are interpolated programs or programs stored in memory 36, may be determined based on the rate of change of the patient parameter value. FIG. 8 is a flow diagram illustrating one technique for determining a rate of change between which processor 34 may control the change in therapy between two therapy programs.

Processor 34 stores a first patient parameter value in memory 36 (90), such as within the current parameters 52 section (FIG. 3) of memory 36. The first patient parameter value may be, for example, the current parameter value associated with the therapy program currently implemented by therapy module 32. The first patient parameter value is not necessarily permanently stored in memory 36, but rather, in some embodiments, memory 36 may include a buffer in which the first patient parameter value may be temporarily stored. Processor 34 monitors the signal from sensor 40 and determines whether the patient parameter value changes (92). Upon detecting a change in the patient parameter value to a second value, processor 34 may store the second patient parameter value in memory 36 (e.g., a buffer within memory 36) (94) along with the first patient parameter value.

Processor 34 may then determine a rate of change of the patient parameter value between the first and second values over time (96). For example, processor 34 may determine the duration of time between the occurrence of the first and second parameter values, such as by determining the difference in time in which the first and second parameter values were each stored in memory 36, and divide the difference between the first and second parameter values by the determined duration in time. In other words, processor 34 "plots" the parameter values over time and determines the slope in the plot between the first and second parameter values. As applied to an accelerometer output, e.g., an electrical signal, processor 34 may determine a rate of change of the amplitude of the electrical signal over time in order to determine the rate of change of the patient parameter value. In this way, the electrical signal from an accelerometer may be directly used to determine a rate of adjusting therapy between two or more therapy programs. Output of other sensors may also be directly used by processor 34 to determine a rate of changing between two therapy programs.

After determining the rate of change between the first and second parameter values over time (96), processor 34 may control therapy module to shift between a therapy program associated with the first patient parameter value to a therapy program associated with the second patient parameter value (either from table 70 or interpolated based on programs within table 70) based on the determined rate of change. In embodiments in which electrical stimulation is shifted between two electrodes via interleaving signals, the signals may be interleaved via the determined rate of change. In embodiments in which electrical stimulation is ramped up and down between two electrodes, the determined rate of change may determine the rate at which the ramping of current is performed.

In other embodiments, processor 34 may utilize a rate of change to shift between two therapy programs that is based on the rate of change between the first and second patient parameter values, but is not proportionate to the rates of change. For example, processor 34 may determine the rate of change between the first and second patient parameter values and utilize a look-up function to find a corresponding rate of change for shifting between two therapy programs. The former approach of basing the rate of change for shifting between two therapy programs on the rate of change between two patient parameter values, rather than adopting the rate of change between the patient parameter values, may be useful for personalizing the rate of change to a particular patient. In some cases, different patients may prefer different techniques for shifting between two therapy programs. Accordingly, a clinician may determine what a patient's preference as to the rate of change for shifting between two programs and how it is related to the rate of change between two parameter values. The patient's preference as to the rate of change for shifting between two programs may be correlated to a rate of change between two patient parameter values during a trial period, prior to programming IMD 12 for delivery of chronic therapy.

In some embodiments, the rate of adjusting between two therapy programs may be based on a rate of change between two or more patient parameter values. For example, an average or mean of a first rate of change based on a first patient parameter value and a second rate of change based on a second patient parameter value may determine the actual rate of change implemented by processor 34 to shift between two therapy programs. Alternatively, the first rate of change may be validated based on the second rate of change (i.e., is the second rate of change substantially similar to the first rate of change?). In one embodiment, the first rate of change may be based on patient posture, which may be determined based on one or more accelerometer signals, while a second rate of change is based on another physiological parameter that varies as a function of patient activity (e.g., respiration rate, heart rate, etc.). In another embodiment, both the first and second rates of change may be based on patient posture, where the first rate of change is based on a signal from a first accelerometer and the second rate of change is based on a signal from a second accelerometer. Use of more than one patient parameter to determine a rate of adjusting between therapy programs may provide a robust algorithm for determining the rate of change (or "adjustment"). In other embodiments, a rate change of any number of patient parameters may be considered when determining an actual rate for adjusting between two or more therapy programs.

When delivering therapy from IMD 12 based on therapy information/patient parameter value associations, there may be a delay, or "lag," prior to identifying a substantially constant patient parameter value because the patient parameter value may change as patient 14 transitions from one physiological condition to another. For example, when patient 14 transitions from a recumbent posture to a standing posture, a large number of patient parameter values that are changing may be detected when patient 14 is in a posture between the recumbent and standing postures. Thus, when the patient parameter is rapidly changing, e.g., when the patient is quickly transitioning between activities or postures, the therapy may be inappropriate for a short period of time prior to identifying the correct therapy information. Inappropriate therapy may cause, for example, patient discomfort. As described in commonly-assigned U.S. Patent Application Publication No. 2007/0150029 by Bourget et al., entitled, "CLOSED-LOOP THERAPY ADJUSTMENT" and filed on Dec. 1, 2006, IMD 12 may instead deliver a predetermined, default, therapy according a known safe mode program, or suspend therapy, during times in which the patient parameter is rapidly and/or transiently changing in order to avoid delivering inappropriate therapy. The safe mode is a set of parameters that is known to provide a safe and comfortable therapy to patient 14 from IMD 12. For example, the safe mode for an implanted electrical stimulator may be to set the stimulation amplitude to 0 volts. This would effectively turn off the stimulation and remove any undesirable side effects of the therapy.

For some therapies and patients, however, turning off the therapy may not be safe or comfortable. In the example of an implanted neurostimulator, the safe mode for patient 14 may be a specific combination of therapy parameters that yield a safe and comfortable therapy setting. In some embodiments, the safe mode is a preconfigured setting or a rollback to a last or last-known safe and comfortable therapy state. For an implantable drug delivery device, the safe mode setting may involve a user-predefined rate which takes into account the possibilities of drug concentration change, tube-set, and/or other variables.

In some embodiments, the safe mode may be defined by allowing patient 14, a clinician, a caregiver, or another qualified individual to save one or more safe therapy configurations that provide patient 16 with safe and comfortable therapy. In other embodiments, IMD 12 may determine the therapy parameters of the safe mode, such as by implementing an algorithm that configures the safe mode based on a last known therapy program, which includes one or more therapy parameters, that yielded safe and comfortable therapy to patient 16. Patient 16, a clinician, a caregiver, or another qualified individual may have the ability to rollback to any of the safe mode configurations for IMD 12 as desired.

The safe mode may be patient, therapy, and/or clinician specific. In some embodiments, one safe mode configuration may be used for all patients who receive a certain type of treatment. For example, the safe mode for a drug delivery device may involve suspending drug delivery. In this embodiment, the patient may be alerted when IMD 12 enters safe mode and may be instructed to take oral medications until therapy is restored. In other embodiments, a clinician may use a specific safe mode for all patients. For example, the safe mode may be set to fifty percent of a last-known therapy. In yet other embodiments, the safe mode may be specific to the individual patient 14 and customizable based on the needs and symptoms of patient 14.

Figure 9:
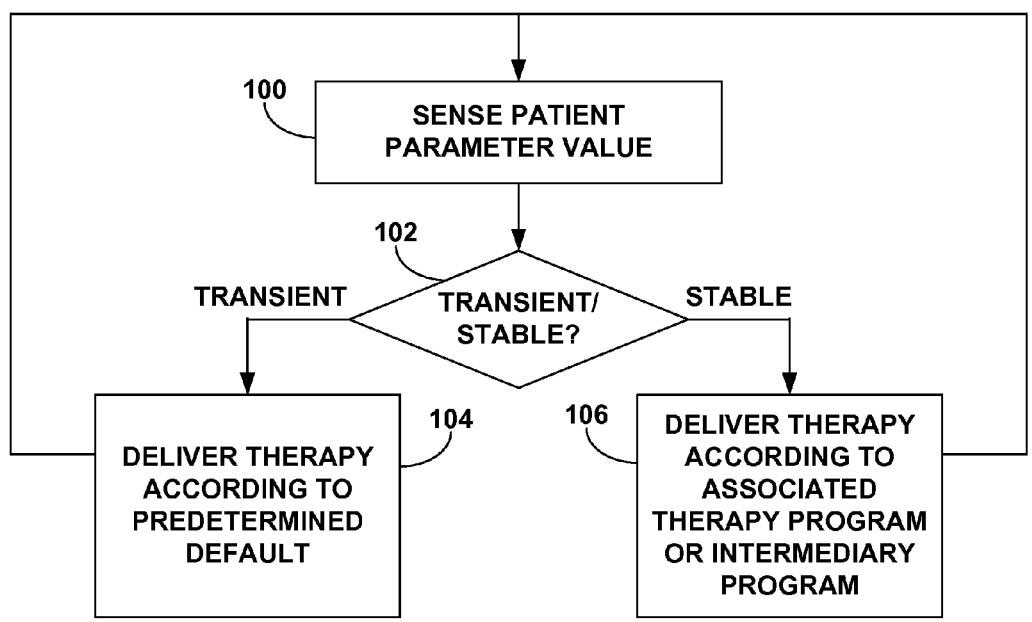
FIG. 9 is a flow diagram illustrating an example technique for delivering therapy according to a stored or intermediate therapy program or a predetermined default based on whether sensed patient parameter values are stable or transient.

For example, according to the example of FIG. 9, processor 34 senses the one or more patient parameter values (100). Processor 34 then determines whether the patient parameter values are transient or stable (102). For example, processor 34 may determine whether the rate of change of the patient parameter values exceeds a threshold.

If the patient parameter is transient, e.g., rapidly changing, processor 34 controls delivery of therapy according to predetermined, default therapy information, which may include low values for therapy parameters such as amplitude, pulse width, or pulse rate, for a predetermined period of time (104). In other embodiments, the predetermined, default therapy information may cause processor 34 to suspend delivery of therapy for a period of time. The predetermined period of time may be chosen such that the patient parameter is likely to be stable at the end of the period, e.g., the patient is likely to be stable within the new posture or activity. If the patient parameter value is stable, e.g., the rate of change is below the threshold, processor 34 may control delivery of therapy according to a therapy program associated with the stable patient parameter value in the table or generating an intermediate program by interpolating between a most recently implemented therapy program and a stored therapy program (106).

As previously described, one or more internal and/or external sensors may be used to monitor one or more patient parameter values and IMD 12 may adjust a therapy program based on a sensed patient parameter value. For example, in the case of SCS that is delivered to treat pain, the posture of the patient may affect the lead placement relative to the target tissue sites. The lead placement may affect the efficacy of therapy delivered to the patient. Thus, in some cases, it may be desirable to adjust one or more therapy parameters (e.g., switch between therapy programs) in order to optimize the efficacy of therapy delivery in response to patient posture changes. In addition to posture, the patient parameter may include activity, heart rate, respiration rate, respiratory volume, core temperature, blood pressure, blood oxygen saturation, partial pressure of oxygen within blood, partial pressure of oxygen within cerebrospinal fluid, muscular activity, arterial blood flow, electromyogram (EMG), an electroencephalogram (EEG), an electrocardiogram (ECG) or galvanic skin response.

Figure 10:
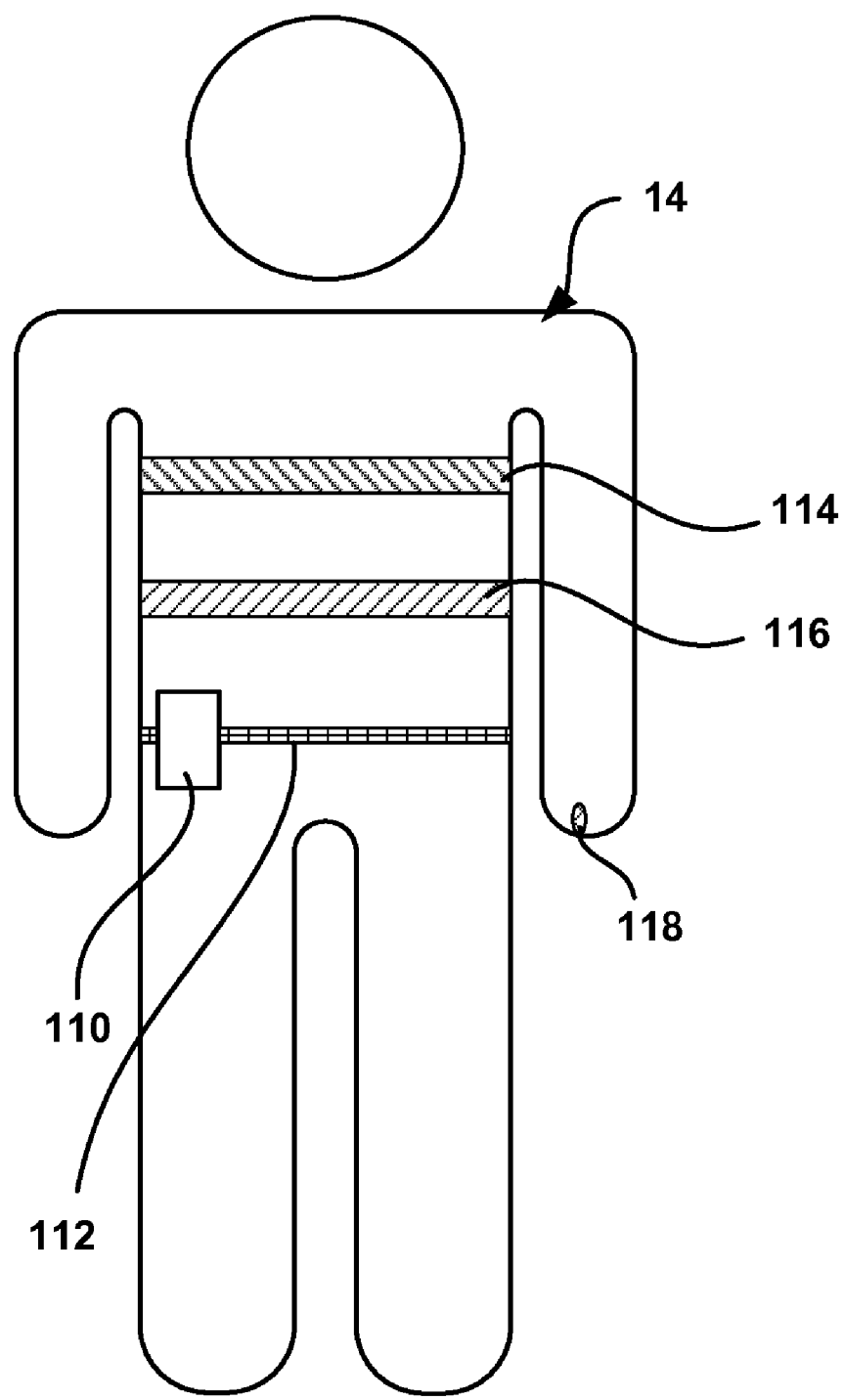
FIG. 10 is a schematic diagram of embodiments of external activity sensing devices that may be used to determine a patient parameter value.

FIG. 10 is a schematic diagram illustrating external sensing device 110 that may be used to monitor a patient parameter, such as a posture, activity level, respiration rate or ECG, of patient 14. Signals generated by external sensing device 110 may be sent to IMD 12 or programmer 20 via wireless signals or a wired connection. IMD 12 or programmer 20 may implement the signals from external sensing device 110 in a closed-loop therapy adjustment technique, as described above. Activity sensing device 110 is an external device that may be attached to patient 14 via a belt 112. Alternatively, activity sensing device 110 may be attached to patient 14 by any other suitable technique, such as a clip that attaches to the patient's clothing, or activity sensing device 110 may be worn on a necklace that is worn around the patient's neck or a watch on the patient's wrist. Activity sensing device 110 may include a sensor that generates a signal indicative of patient motion, such as accelerometer or a piezoelectric crystal. If activity sensing device 110 includes a sensor that senses relative motion, such as an accelerometer, it may be desirable to attach sensing device 110 to a torso of patient 14 in order to gather the most relevant activity data.

In addition to or instead of a motion sensor, external sensing device 110 may include or be coupled to a sensor that generates a signal that indicates a physiological parameter that varies as a function of patient activity, which may be used to determine an activity level of patient 14. As described above, suitable physiological parameters include heart rate, respiratory rate, ECG morphology, respiration rate, respiratory volume, core temperature, a muscular activity level, subcutaneous temperature or electromyographic activity of patient 14. For example, in some embodiments, patient 14 may wear an ECG belt 114 that incorporates a plurality of electrodes for sensing the electrical activity of the heart of patient 14. The heart rate and, in some embodiments, ECG morphology of patient 14 may monitored based on the signal provided by ECG belt 114. Examples of suitable ECG belts for sensing the heart rate of patient 14 are the "M" and "F" heart rate monitor models commercially available from Polar Electro. In some embodiments, instead of ECG belt 114, patient 14 may wear a plurality of ECG electrodes (not shown in FIG. 10) attached, e.g., via adhesive patches, at various locations on the chest of patient 14, as is known in the art. An ECG signal derived from the signals sensed by such an array of electrodes may enable both heart rate and ECG morphology monitoring, as is known in the art.

A respiration belt 116 that outputs a signal that varies as a function of respiration of the patient may also be worn by patient 14 to monitor activity to determine whether patient 14 is undertaking activity or a change in posture for which a therapy programming change may be desirable. Respiration belt 116 may be a plethysmograpy belt, and the signal output by respiration belt 116 may vary as a function of the changes is the thoracic or abdominal circumference of patient 14 that accompany breathing by patient 14. An example of a suitable respiration belt is the TSD201 Respiratory Effort Transducer commercially available from Biopac Systems, Inc. Alternatively, respiration belt 116 may incorporate or be replaced by a plurality of electrodes that direct an electrical signal through the thorax of patient 14, and circuitry to sense the impedance of the thorax, which varies as a function of respiration of patient 14, based on the signal. In some embodiments, the ECG and respiration belts 114, 116 may be a common belt worn by patient 14.

Patient 14 may also wear transducer 118 that outputs a signal as a function of the oxygen saturation of the blood of patient 14. Transducer 118 may be an infrared transducer. Transducer 118 may be located on one of the fingers or earlobes of patient 14. Each of the types of sensors 110, 114, 116, and 118 described above may be used alone or in combination with each other, as well as in addition to or instead of sensor 40 (FIG. 2) located within IMD 12.

Various embodiments have been described. However, one of ordinary skill in the art will understand that various modifications may be made to the described embodiments without departing from the scope of the disclosure. For example, although described with reference to techniques for automatically populating a table of patient parameter values and associated therapy programs, the disclosure is not so limited. Programs may be associated with sensed patient parameter values by any technique, including manual programming by, for example, a clinician. In addition, although to interpolating between two therapy programs and determining a rate of adjusting between two therapy programs were primarily described in the embodiments above as being performed by processor 34 of IMD 12, in other embodiments processors of other devices, such as a processor of programmer 20 (FIG. 1) may interpolate between programs and determine a rate of changing between two programs. In addition, the sensors that generate the signals indicative of patient parameter values may be external to patient 14 or implanted within patient 14. The use of external sensors or sensors otherwise separate from IMD 12 may allow IMDs already implanted within a patient to be retrofit to include the therapy program interpolation and rate of adjustment features described herein.

These and other embodiments are within the scope of the following claims.

The invention claimed is:

1. A method comprising:
sensing a first value of a parameter of a patient;
delivering therapy to the patient according to a first therapy parameter value associated with the first value of the patient parameter in a data structure comprising a plurality of patient parameter values and associated therapy parameter values;
detecting a change from the first value of the patient parameter to a second value of the patient parameter;
identifying a third value of the patient parameter within the data structure that is closest to the second value of the patient parameter, wherein the third value of the patient parameter is associated with a second therapy parameter value within the data structure; and
determining an intermediate therapy parameter value that provides efficacious therapy to the patient when the second value of the patient parameter is observed by interpolating the therapy parameter between the first and second therapy parameter values.

2. The method of claim 1, further comprising comparing a difference between the second and third values of the patient parameter to a threshold value, wherein determining the intermediate therapy parameter value comprises determining the intermediate therapy parameter value if the difference between the second and third values of the patient parameter is greater than the threshold value.

3. The method of claim 1, further comprising delivering the therapy according to the intermediate therapy parameter value.

4. The method of claim 3, further comprising delivering the therapy according to the intermediate therapy parameter value until a change in the parameter of the patient is detected.

5. The method of claim 3, further comprising delivering the therapy according to the second therapy parameter value after delivering the therapy according to the intermediate therapy parameter value.

6. The method of claim 3, further comprising delivering the therapy according to the first therapy parameter value after delivering the therapy according to the intermediate therapy parameter value.

7. The method of claim 1, wherein the first, second, and intermediate therapy parameter values each comprise a respective value of at least one of an electrode configuration, an electrical stimulation pulse rate, an electrical stimulation pulse width, an electrical stimulation current amplitude, a fluid delivery dosage, a cycle of therapy delivery, a rate of change of the electrical stimulation current amplitude, or a fluid delivery rate.

8. The method of claim 1, wherein the parameter of the patient comprises a posture of the patient.

9. The method of claim 1, wherein the parameter of the patient comprises at least one of activity, heart rate, respiration rate, respiratory volume, core temperature, blood pressure, blood oxygen saturation, partial pressure of oxygen within blood, partial pressure of oxygen within cerebrospinal fluid, muscular activity, arterial blood flow, electromyogram (EMG), an electroencephalogram (EEG), an electrocardiogram (ECG), or galvanic skin response.

10. The method of claim 1, further comprising determining a first rate of the change from the first patient parameter value to the second patient parameter value, wherein delivering the therapy according to the intermediate therapy parameter value comprises adjusting the delivery of the therapy to the patient from the first therapy parameter value to the intermediate therapy parameter value at a second rate based on the first rate.

11. The method of claim 10, wherein the second rate of change is substantially equal to the first rate of change.

12. The method of claim 1, further comprising:
determining whether the second value of the patient parameter is stable;
delivering therapy according to the intermediate therapy parameter value if the second value is stable; and
delivering therapy according to a safe mode or suspending therapy if the second value is not stable.

13. A system comprising:
a medical device that is configured to deliver a therapy to a patient;
a sensor that is configured to sense a patient parameter of the patient;
a memory that stores a data structure comprising a plurality of patient parameter values and associated therapy parameter value; and
a processor configured to control the medical device to deliver the therapy to the patient according to a first therapy parameter value associated with a first value of the patient parameter sensed via the sensor, detect a change in the first value to a second value of the patient parameter sensed via the sensor, identify a third value of the patient parameter within the data structure that is closest to the second value, wherein the third value is associated with a second therapy parameter value within the data structure, and interpolate the therapy parameter between the first and second therapy parameter values to determine an intermediate therapy parameter value that provides efficacious therapy to the patient when the second value of the patient parameter is observed.

14. The system of claim 13, wherein the processor compares a difference between the second and third values of the patient parameter to a threshold value, and determines the intermediate therapy parameter value if the difference between the second and third values of the patient parameter is greater than the threshold value.

15. The system of claim 13, wherein the therapy parameter values each comprise respective values of at least one of an electrode configuration, an electrical stimulation pulse rate, an electrical stimulation pulse width, an electrical stimulation current amplitude, a fluid delivery dosage, a cycle of therapy delivery, a rate of change of the electrical stimulation current amplitude, or a fluid delivery rate.

16. The system of claim 13, wherein the patient parameter comprises a posture of the patient.

17. The system of claim 13, wherein the patient parameter comprises at least one of activity, heart rate, respiration rate, respiratory volume, core temperature, blood pressure, blood oxygen saturation, partial pressure of oxygen within blood, partial pressure of oxygen within cerebrospinal fluid, muscular activity, arterial blood flow, electromyogram (EMG), an electroencephalogram (EEG), an electrocardiogram (ECG), or galvanic skin response.

18. The system of claim 13, wherein the processor is configured to control the medical device to deliver the therapy according to the intermediate therapy parameter value.

19. The system of claim 13, wherein the processor further determines a first rate of the change from the first patient parameter value to the second patient parameter value and controls the medical device to adjust the delivery of the therapy to the patient from the first therapy parameter value to the intermediate therapy parameter value at a second rate based on the first rate.

20. The system of claim 19, wherein the second rate is substantially equal to the first rate.

21. The system of claim 13, wherein the processor determines whether the second value of the patient parameter is stable prior to determining the intermediate therapy parameter value, delivers therapy according to the intermediate therapy parameter value if the second value is stable, and delivers therapy according to a safe mode or suspends therapy if the second value is not stable.

22. A non-transitory computer-readable medium comprising instructions that cause a processor to control a therapy delivery device to:
deliver therapy to the patient according to a first therapy parameter value associated with a first value of the patient parameter in a data structure comprising a plurality of patient parameter values and associated therapy parameter values;
detect a change from the first value of the patient parameter to a second value of the patient parameter;
identify a third value of the patient parameter within the data structure that is closest to the second value, wherein the third value is associated with a second therapy parameter value within the data structure; and
determine an intermediate therapy parameter value that provides efficacious therapy to the patient when the second value of the patient parameter is observed by interpolating the therapy parameter between the first and second therapy parameter values.

23. The computer-readable medium of claim 22, further comprising instructions that cause the programmable processor to compare a difference between the second and third values of the patient parameter to a threshold value, wherein the instructions cause the programmable processor to determine the intermediate therapy parameter value if the difference between the second and third values of the patient parameter is greater than the threshold value.

24. A system comprising:
means for delivering therapy to the patient according to a first therapy parameter value associated with the first value of the patient parameter in a data structure comprising a plurality of patient parameter values and associated therapy parameter values;
means for detecting a change from the first value of the patient parameter to a second value of the patient parameter;
means for identifying a third value of the patient parameter within the data structure that is closest to the second value of the patient parameter, wherein the third value of the patient parameter is associated with a second therapy parameter value within the data structure; and
means for determining an intermediate therapy parameter value that provides efficacious therapy to the patient when the second value of the patient parameter is observed by interpolating the therapy parameter between the first and second therapy parameter values.

25. The system of claim 24, further comprising means for comparing a difference between the second and third values of the patient parameter to a threshold value, wherein the means for determining the intermediate therapy parameter value determines the intermediate therapy parameter value if the difference between the second and third values of the patient parameter is greater than the threshold value.

* * * * *